US012770721B2

(12) United States Patent
Alperin

(10) Patent No.: US 12,770,721 B2
(45) Date of Patent: Oct. 20, 2026

(54) APPARATUS AND A METHOD FOR GENERATING A DIAGNOSTIC REPORT

(71) Applicant: SurvivorNet, Inc., New York, NY (US)

(72) Inventor: Steven David Alperin, New York, NY (US)

(73) Assignee: SurvivorNet, Inc., New York, NY (US)

( * ) Notice: Subject to any disclaimer, the term of this patent is extended or adjusted under 35 U.S.C. 154(b) by 66 days.

(21) Appl. No.: 18/789,047

(22) Filed: Jul. 30, 2024

(65) Prior Publication Data

US 2025/0191713 A1 Jun. 12, 2025

Related U.S. Application Data

(63) Continuation of application No. 18/536,623, filed on Dec. 12, 2023, now Pat. No. 12,073,930.

(51) Int. Cl.
*G16H 15/00* (2018.01)
*G06N 20/00* (2019.01)

(52) U.S. Cl.
CPC ............. *G16H 15/00* (2018.01); *G06N 20/00* (2019.01)

(58) Field of Classification Search
CPC ............................... G16H 15/00; G16H 50/30
See application file for complete search history.

(56) References Cited

U.S. PATENT DOCUMENTS

2019/0206517 A1* 7/2019 Devarakonda ......... G16H 50/70
2019/0385711 A1 12/2019 Shriberg et al.
2020/0184209 A1* 6/2020 Flerlage ............... G06V 30/414

FOREIGN PATENT DOCUMENTS

IN 202211049048 A 9/2022
WO 2021247557 A1 12/2021
WO 2022212765 A1 10/2022
WO WO-2024259032 A2 * 12/2024 ............ G16H 20/70

OTHER PUBLICATIONS

Yang, Zhan, Wei Xu, and Runyu Chen. "A deep learning-based multi-turn conversation modeling for diagnostic Q&A document recommendation." Information processing & management 58.3 (2021): 102485. (Year: 2021).*

* cited by examiner

*Primary Examiner* — Constantine Siozopoulos
(74) *Attorney, Agent, or Firm* — CALDWELL LLC

(57) ABSTRACT

An apparatus for generating a diagnostic report is disclosed. The apparatus includes at least a processor and a memory communicatively connected to the at least a processor. The memory instructs the processor to receive a user profile from a user. The memory instructs the processor to generate a first set of inquiries as a function of the user profile using an inquiry machine learning model. The memory instructs the processor to receive a first set of inquiry responses from the user as a function of the first set of inquiries. The memory instructs the processor to generate a diagnostic report as a function of the first set of inquiries and the first set of inquiry responses. The memory instructs the processor to display the diagnostic report using a display device.

20 Claims, 9 Drawing Sheets

APPARATUS AND A METHOD FOR GENERATING A DIAGNOSTIC REPORT

CROSS-REFERENCE TO RELATED APPLICATIONS

This application is a continuation of Non-provisional application Ser. No. 18/536,623 filed on Dec. 12, 2023, and entitled "APPARATUS AND A METHOD FOR GENERATING A DIAGNOSTIC REPORT," the entirety of which is incorporated herein by reference.

FIELD OF THE INVENTION

The present invention generally relates to the field of artificial intelligence. In particular, the present invention is directed to an apparatus and a method for generating a diagnostic report.

BACKGROUND

Data and memory management for machine-learning models is an issue that has hampered their ability. Machine-learning models have a limit on the amount of data that can be received as input in the form of a prompt. Solutions to carefully manage and select the data that is input into machine-learning models are needed in order to increase the efficiency of their use.

SUMMARY OF THE DISCLOSURE

In an aspect, an apparatus for generating a diagnostic report is disclosed. The apparatus includes at least a processor and a memory communicatively connected to the at least a processor. The memory instructs the processor to receive a user profile pertaining to a user. The memory instructs the processor to extract contextual data from the user profile and generate a set of inquiries as a function of the contextual data using an inquiry machine learning model. Generating the first set of inquiries includes training the inquiry machine learning model using inquiry training data, wherein the inquiry training data includes a plurality of contextual data as input correlated to the a plurality of inquiries as output. The memory instructs the processor to receive a set of inquiry responses from the user as a function of the set of inquiries. The memory instructs the processor to generate a diagnostic report as a function of the set of inquiries and the set of inquiry responses. The memory instructs the processor to display the diagnostic report using a display device.

In another aspect, a method for generating a diagnostic report is disclosed. The method include receiving, using the at least a processor, a user profile from a user. The method includes extracting, using the at least a processor, contextual data from the user profile. The method includes generating, using the at least a processor, a set of inquiries as a function of the contextual data using an inquiry machine learning model. Generating the set of inquiries includes training the inquiry machine learning model using inquiry training data, wherein the inquiry training data includes a plurality of contextual data as input correlated to a plurality of inquiries as output. The method includes receiving, using the at least a processor, a set of inquiry responses from the user as a function of the set of inquiries. The method includes generating, using the at least a processor, a diagnostic report as a function of the set of inquiries and the set of inquiry responses. The method includes displaying the diagnostic report using a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for generating a diagnostic report is disclosed. The apparatus includes at least a processor and a memory communicatively connected to the at least a processor. The memory instructs the processor to receive a user profile from a user. The memory instructs the processor to generate a first set of inquiries as a function of the user profile using an inquiry machine learning model. Generating the first set of inquiries includes generally training the inquiry machine learning model using a non-user specific training data. Additionally, generating the first set of inquiries includes specifically training the inquiry machine learning model using inquiry training data, wherein the inquiry training data includes a plurality of user profiles as inputs correlated to the first set of inquiries as outputs. The memory instructs the processor to receive a first set of inquiry responses from the user as a function of the first set of inquiries. The memory instructs the processor to generate a diagnostic report as a function of the first set of inquiries and the first set of inquiry responses. The memory instructs the processor to display the diagnostic report using a display device. Exemplary embodiments illustrating aspects of the present disclosure are described below in the context of several specific examples.

Figure 1:
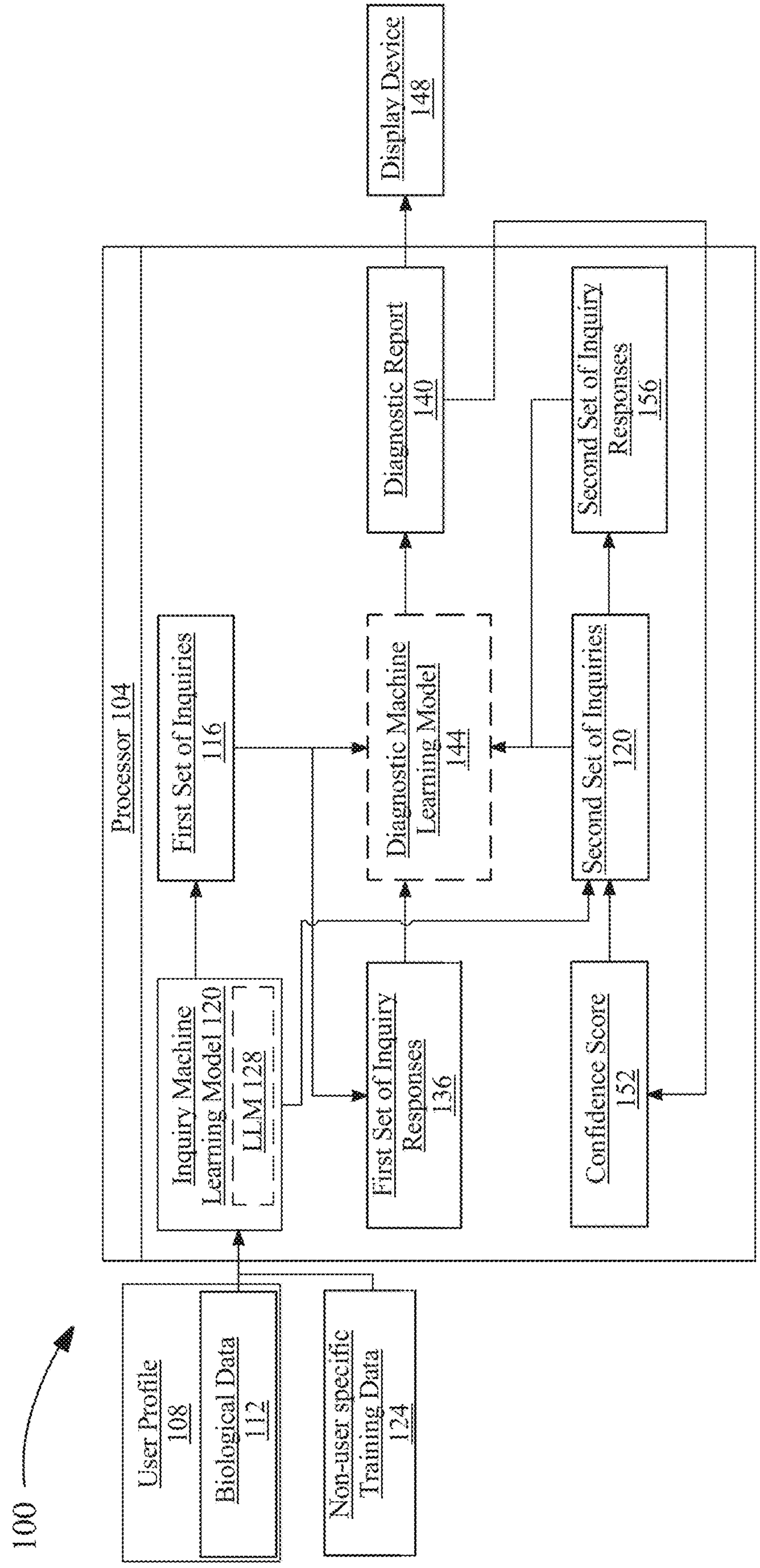
FIG. 1 is a block diagram of an exemplary embodiment of an apparatus for generating a diagnostic report.

Referring now to FIG. 1, an exemplary embodiment of an apparatus 100 for generating a diagnostic report is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may be configured to receive a user profile 108 from a user. For the purposes of this disclosure, a "user profile" is a representation of information and/or data associated with a user. A user profile 108 may be made up of a plurality of user data. As used in the current disclosure, "user data" is information associated with the user. A user profile 108 may be created by a processor 104, a user, medical professional, or a third party. The user profile 108 may include any of the following personal information: age, weight, height, gender, geographical location, insurance information, medical history, marital status, familial medical history, and the like. A user profile 108 may include biological data 112. used in the current disclosure, "biological data" is data related to a user's health. This may include current and historical versions of data related to the user's health. Biological data 112 may provide insights into the functioning and health of biological systems. The collection and analysis of biological data are crucial in medicine, healthcare, research, and sports science, among other fields. Biological data may include information regarding any of the user organs. This may include the user heart, liver, lungs, brain, bones, pancreas, reproductive organs, liver, skin, blood, digestive tract, and the like. Biological data may include information such as heart rate, blood pressure, body temperature, Respiratory Rate, Blood oxygen saturation, electrocardiograms, electromyogram, electroencephalogram. Biological data 112 may include chemical, biological, physical, and behavioral data relating to a user. Biological data 112 may include information regarding a user's health including medical history, user diet, exercise, sleep, family medical history, and the like. In other embodiments, biological data 112 may include information collected from a standard health screening such as X-rays, MRI, blood test, lab tests, examinations, and the like.

With continued reference to FIG. 1, biological data 112 may be extracted from a user using at least a sensor. As used in this disclosure, a "sensor" is a sensor device that produces an electrical output signal for purpose of sensing and monitoring biological events or changes in its environment. In some cases, In some embodiments, the sensor may include one or more processors that perform one or more processing steps as described in this disclosure. In some cases, the sensor may include, without limitation, a temperature sensor, EMG sensor, ECG sensor, airflow sensor, glucometer sensor, pressure sensor, acoustic sensor, image sensor, magnetic field sensor, and the like thereof. In some embodiments, without limitation, the sensor may include a physical sensor, wherein the physical sensor is a device that measures a physical quantity. In some cases, the sensor may convert physical quantity into an output signal which can be read by processor 104. In some embodiments, without limitation, sensor may include a chemical sensor, wherein the chemical sensor is a device that converts a property of a particular analyte into a measurable signal that is proportional to the analyte concentration. In some cases, a chemical sensor may recognize an analyte molecule in a selective way by transforming it into an analytical electrical signal. In some cases, analyte concentration may include, without limitation, PH value, Ca+ concentration, the glucose concentration of body liquid and the like thereof. In some embodiments, without limitation, sensor may include a biosensor, wherein the biosensor is a device that combine biological material with a suitable platform for a detection of pathogenic organisms, carcinogenic, mutagenic, toxic chemicals or for reporting a biological effect. In some cases, a sensor may include, without limitation, a biosensor, electrochemical biosensor, physical biosensor, optical biosensor, wearable biosensor, and the like thereof.

With continued reference to FIG. 1, a processor 104 may extract biological data 112 from a user using a wearable device. As used in the current disclosure, a "wearable device" is a computing device that is designed to be worn on a user's body or clothing. The wearable device may detect biological data 112, user data, or wearable device data. In embodiments, a wearable device may include a smart watch, smart ring, fitness tracking device, and the like. As used in the current disclosure, "wearable device data" is data collected by a wearable device. Wearable device data may include data and associated analysis corresponding to, for instance and without limitation, accelerometer data, pedometer data, gyroscope data, electrocardiogramata, electrooculography (EOG) data, bioimpedance data, blood pressure and heart rate monitoring, oxygenation data, biosensors, fitness trackers, force monitors, motion sensors, video and voice capture data, social media platform data, and the like. User profile 108 may be provided by a user or a second individual on behalf of a user, for instance and without limitation a physician, medical professional, nurse, hospice care worker, mental health professional, and the like. User profile 108 may originate from a user questionnaire, graphical user interface (GUI), or any other suitable forum for gathering information regarding biological data 112. Persons skilled in the art, upon review of this disclosure in its entirety, will be aware of the various ways in which biological data 112 may be collected and provided to the system described herein.

With continued reference to FIG. 1, a user profile 108 may be received by processor 104 via user input. For example, and without limitation, the user or a third party may manually input user profile 108 using a user interface 304 or 308 or a remote device, such as for example, a smartphone or laptop. The user profile 108 may additionally be generated via the answer to a series of questions. The series of questions may be implemented using a chatbot, as described herein below. A chatbot may be configured to generate questions regarding any element of the user profile 108. In a non-limiting embodiment, a user may be prompted to input specific information or may fill out a questionnaire. In another embodiment, a user may be prompted to input specific information using drop down menus, check boxes, and the like. In an additional embodiment, a graphical user interface may display a series of questions to prompt a user for information pertaining to the user profile 108. The user profile 108 may be transmitted to processor 104, such as via a wired or wireless communication, as previously discussed in this disclosure. The user profile 108 can be retrieved from multiple sources third-party sources including the user's inventory records, financial records, human resource records, past user profiles 108, sales records, user notes and observations, and the like. A user profile may be placed through an encryption process for security purposes.

With continued reference to FIG. 1, a user profile 108 may include user records. As used in the current disclosure, a "user record" is a document that contains information regarding the user. User records may include medical records, medical history, medical tests, user credentials, doctors notes, previous diagnostic reports, medical imaging documents, insurance information, and government records (i.e. birth certificates, social security cards, and the like). User records may be identified using a web crawler. User records may include a variety of types of "notes" entered over time by the user, medical providers, third-parties, medical professionals, and the like. User records may be converted into machine-encoded text using an optical character reader (OCR).

Still referring to FIG. 1, in some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases. a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2, 4, and 5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, user profile 108 may be generated using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the user profile 108 and biological data 112. The web crawler may be seeded and/or trained with a reputable website, such as the user's medical providers website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract user records, past user profiles 108, notes, and observations, based on criteria such as a time, location, and the like.

With continued reference to FIG. 1, processor 104 may be configured to receive a user profile 108 using an application programming interface (API). As used herein, an "application programming interface" is a set of functions that allow applications to access data and interact with external software components, operating systems, or microdevices, such as another web application or computing device. An API may define the methods and data formats that applications can use to request and exchange information. APIs enable seamless integration and functionality between different systems, applications, or platforms. An API may deliver a user profile 108 to apparatus 100 from a system/application that is associated with a user or other third party custodian of user information. An API may be configured to query for web applications or other websites to retrieve a user profile 108 or other data associated with the user. An API may be further configured to filter through web applications according to a filter criterion. In this disclosure, "filter criterion" are conditions the web applications must fulfill in order to qualify for API. Web applications may be filtered based off these filter criterion. Filter criterion may include, without limitation, web application dates, web application traffic, web application types, web applications addresses, and the like. Once an API filters through web applications according to a filter criterion, it may select a web application. Processor 104 may transmit, through the API, user data include a user profile 108 to apparatus 100. API may further automatically fill out user entry fields of the web application with the user credentials in order to gain access to the user profile 108. Web applications may include, without limitation, a social media website, an online form, file scanning, email programs, third party websites, governmental websites, or the like.

With continued reference to FIG. 1, processor 104 may be configured to extract a plurality of contextual data from the user profile 108. As used in the current disclosure, "contextual data" refers to additional information or details that provide a more comprehensive understanding of a current situation. This additional information helps in interpreting and making sense of the user profile 108 in a specific context. Contextual data may be essential for accurately analyzing, utilizing, and deriving insights from a dataset. Contextual data may be directly relevant to a particular situation, event, or entity. It provides the necessary background and details to understand the data's significance in that specific context. In some cases, contextual data may be used to provide temporal context to a user query or the user dataset. This may include timestamps, time of day, day of the week, or any other temporal details that help establish when the data was generated or relevant to a particular moment. This may include the order/timing in which events or queries occurred. Additionally, a temporal context of the data may be taken as it relates to the timeframe of recent test and lab results. Recent laboratory test results, imaging reports, pathology results, and other diagnostic data may play a role contextualizing the model with this data enables it to correlate symptoms with actual test findings. In additional embodiment, the user adherence or failure to adhere to previous instructions by a medical practitioner may provide additional context to the user profile. This may include details of medications being taken, their dosages, frequency, and adherence to prescribed medication plans. Understanding the user's medication regimen is vital for ensuring appropriate advice and considering potential interactions. In some cases, contextual data may refer to information regarding a user's dietary and lifestyle choices. Information about dietary habits, exercise routines, smoking or alcohol consumption, sleep patterns, and stress levels. Lifestyle factors may provide the model with additional context for the user profile 108. For instance, a user who consumes excessive an amount of alcohol or other controlled substances may provide context to the user's issues involving the kidney, liver, and the like.

With continued reference to FIG. 1, contextual data may be used to provide understanding that the user or entity associated with the data is a critical part of contextual information. This may encompass user profiles, demographics, preferences, historical interactions, and behavioral patterns. In some cases, contextual data may be specific to a user chosen profession. For example, if the user has a profession that requires them to sit at a desk (i.e. Secretary, Lawyer, Financial professional, and the like.) processor 104 may infer that the user may live a more sedimentary life style as compared to a user with a non-sedimentary job (i.e. Construction Woker, Day Laborer, Professional Athlete, and the like.). When extracting the contextual data processor 104 may be configured to place the user dataset through preprocessing steps to clean, transform, and organize the data for further analysis. This could include handling missing values, standardizing formats, and converting unstructured data (e.g., text) into structured representations. In some embodiments, processor may generate contextual data as function of the metadata associated with user profile 108.

With continued reference to FIG. 1, the processor may identify and segregate attributes the user profile 108 that contribute to the contextual understanding of the data. For instance, it could identify temporal attributes (timestamps), spatial attributes (location data), and other user-specific contextual attributes. The processor 104 may then engage in feature engineering, where it transforms the identified attributes into features suitable for analysis. This could involve creating new features, aggregating data, or deriving statistics to capture the context effectively. Depending on the application, the processor 104 may integrate external contextual data sources (e.g., weather data, user profiles, device information) to enrich the contextual understanding. This could involve querying APIs, seeding web crawlers, accessing external databases, and the like. Utilizing the extracted metadata and engineered features, the processor may perform various analyses, such as statistical analysis, machine learning modeling, or data mining, to derive insights and predictions based on the context. The processor 104 combines the insights obtained from the analysis with the identified contextual attributes and metadata to generate contextual data. This could involve creating structured representations that encapsulate both the original data and the derived insights in a way that is understandable and useful.

With continued reference to FIG. 1, processor 104 is configured to generate a first set of inquiries 116 and/or second set of inquiries 120 as a function of the user profile 108 and biological data 112. As used in the current disclosure, a "set of inquiries" is a request or question posed by apparatus 100 seeking information, assistance, or clarification on a specific topic or issue. The inquiry may be formulated using words or phrases that convey what is needed. The first set of inquiries 116 and/or second set of inquiries 120 may be delivered to the user through various mediums, including a chatbot, push notification, email, text message, website, and the like. A first set of inquiries 116 and/or second set of inquiries 120 may be given in the form text, images, verbally, visually, and the like. In an embodiment, the first set of inquiries 116 may be related one or more aspects of the user profile 108 or the biological data 112, as discussed in greater detail here in above. In a non-limiting example, first set of inquiries 116 and/or second set of inquiries 120 may include inquiries related to asking for greater detail for one or more elements of the associated with the user profile 108 or the biological data 112. Non-limiting examples of inquiries that may be included in the first set of inquiries 116 may be "Describe the severity of your symptoms 1-10;" "Describe your symptoms;" "How long have you had these symptoms;" "Do you have pain equally on both sides or just the left/right;" "Do you currently smoke or have smoked in the past;" "Have you ever been diagnosed with cancer;" "Do you have family history of cancer/diabetes/heart problems/high blood pressure;" "How did you get injured;" "Can you raise your arms above your head;" "Please slowly take a deep breath;" and the like. Additionally, the first set of inquiries 116 and/or second set of inquiries 120 may include inquiries asking the user to perform one or more physical tests. The physical tests may include range of motion assessments, strength testing, tenderness and palpation testing, muscle length testing, special orthopedic tests (i.e. Lachman's test, McMurray's test, and the like.) Neurological testing, Balancing and proprioception testing, cardiovascular fitness testing, postural assessments, functional performance testing, pain assessment testing. In some cases, the first set of inquiries 116 and/or second set of inquiries 120 may instruct the user to place one or more medical instruments on their person to facilitate additional medical testing. This may include placing leads for an EKG or VCG, placing a blood pressure cuff to determine blood pressure. In some embodiments, a user may be instructed to place a sensor within their ear, throat, nose, reproductive organs, and the like in order to facilitate testing. Alternatively, first set of inquiries 116 and/or second set of inquiries 120 may include inquiries related specifically to the user. For example, this may include question regarding the caloric intake of the user for a given time period. In some cases, the first set of inquiries 116 and/or second set of inquiries 120 may be provided to the user using a digital avatar, chat bot, verbally, visually, video, and the like. Providing the first set of inquiries 116 and/or second set of inquiries 120 to the user may vairy according to the symptoms or aliments of the user. As compared to the first set of inquiries 116 the second set of inquiries 120 may be a more refined and tailored set of questions targeted at the user's symptoms, user profile 108, responses to the first set of inquiries 116, and the like. Generation of the second set of inquiries 120 will be discussed in greater detail herein below.

With continued reference to FIG. 1, processor 104 may generate the first set of inquiries 116 and/or second set of inquiries 120 using an inquiry machine learning model 124. As used in the current disclosure, a "inquiry machine learning model" is a machine-learning model that is configured to generate a first set of inquiries 116 and/or second set of inquiries 120. Inquiry machine learning model 124 may be consistent with the machine-learning model described below in FIG. 2. Inputs to the inquiry machine learning model 124 may include a user profile 108, biological data 112, historical versions of the first set of inquiries 116, non-user specific training data 128, contextual data, examples of first set of inquiries 116, and the like. Outputs of the inquiry machine learning model 124 may include first set of inquiries 116 or a second set of inquiries 124 tailored to user profile 108 and the contextual data. Inquiry training data may include a plurality of data entries containing a plurality of inputs that are correlated to a plurality of outputs for training a processor by a machine-learning process. In an embodiment, inquiry training data may include the user profile 108 and the background data as inputs correlated to examples of a first set of inquiries 116. Inquiry training data may be received from a database. Alternatively, inquiry training data may be generated using a web crawler, API, look-up table, user input, chatbot, and the like. Inquiry training data may be training data that is specific to the current user. Inquiry training data may contain information about the user's user profile 108, biological data 112, historical versions of the first set of inquiries 116, non-user specific training data 128, contextual data, examples of first set of inquiries 116, and the like. In an embodiment, inquiry training data may be iteratively updated as a function of the input and output results of past inquiry machine learning models 124 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, an inquiry machine learning model 124 may be generally trained using a non-user specific training data 128. As used in the current disclosure, "non-user specific training data" is training data comprised of a vast and diverse dataset. The non-user specific training data may be very large and describe a wide range of topics, styles, and sources. The non-user specific training data 128 may include an excesses of a billion unique words from many sources. This may include textbooks, articles, magazines, physician notes, academic papers, emails, books, websites, forums, social media, and the like. The dataset may be sourced from multiple languages to train multilingual models, encompassing major world languages. The dataset may cover various regional dialects, slangs, and idiomatic expressions to ensure a broad linguistic understanding. Additionally, the dataset may include formal and informal language, technical writing, conversational text, humor, satire, and more. The dataset may spans across genres like science fiction, fantasy, mystery, romance, historical, technical, and more. The non-user specific training data 128 may include detailed information about anatomy, physiology, biological systems, organs, and their functions, aiding in understanding the human body and its complexities. A significant portion of the dataset includes academic papers, articles, and publications from reputable medical journals. This provides the language model with a comprehensive understanding of established medical research and advancements. Non-user specific training data 128 may include de-identified electronic health records from diverse healthcare institutions, encompassing patient demographics, medical history, symptoms, diagnoses, prescribed medications, treatments, and outcomes. The non-user specific training data 128 may include An extensive collection of medical images such as X-rays, MRIs, CT scans, histopathology images, and other diagnostic imaging data. These images are labeled with corresponding diagnoses to help the model learn associations between visual data and medical conditions. In an embodiment, non-user specific training data 128 may include data from clinical trials, including trial design, inclusion/exclusion criteria, treatments, outcomes, and adverse events. This data aids in understanding experimental treatments and their effects. In some cases, non-user specific training data 128 may include pathology reports, lab test results, and other diagnostic data to help the model understand how different tests and markers relate to specific medical conditions. This may include data about pharmaceutical drugs, their mechanisms of action, dosage guidelines, side effects, contraindications, and interactions with other medications. Non-user specific training data 128 may include a vast collection of data outlining various medical diagnoses, procedures, surgical interventions, and their associated details, aiding the model in learning disease patterns and treatment options. Non-user specific training data 128 may include information related to genetic markers, mutations, genomic sequences, and their associations with specific diseases. This assists in understanding the genetic underpinnings of various Non-user specific training data 128 may include data associate with established healthcare guidelines, best practices, and treatment protocols followed by medical professionals in different regions or specialties.

With continued reference to FIG. 1, once processor 104 has received the non-user specific training data the dataset may undergo a preprocessing step to prepare the dataset for use in a machine learning model. This preprocessing step may be configured to remove noise, duplicates, and irrelevant content. Measures are taken to maintain the quality of the data, removing erroneous or misleading information. The preprocessing step may be configured to format and/or structure for data where the data is transformed from an unprocessed format and/or structure into a processed format and/or structure that is prepared for use in the generation and training of an artificial intelligence (AI) model, for example a machine learning model, a neural network, and the like. Preprocessing the dataset may include adding data, replicating data, and the like. In some embodiments, destructive transformation of data may include fixing or removing incorrect, corrupted, incorrectly formatted, duplicate, or incomplete data within a dataset, and the like. In some embodiments, structural transformation of data may include moving and/or combining columns of data in a data set, and the like. The converting of data may include the processing, cleansing, standardizing, and categorizing of data into a cleansed data format for use in generating an accumulated artificial intelligence (AI) model. In an embodiment, preprocessing the dataset may include the processing, cleansing, and standardizing of data into a data set and/or data bucket for use in generating an artificial intelligence model.

Still referring to FIG. 1, an inquiry machine learning model 124 may include a large language model (LLM). A "large language model," as used herein, is a deep learning algorithm that can recognize, summarize, translate, predict and/or generate text and other content based on knowledge gained from massive datasets. Large language model may be trained on large sets of data; for example, non-user specific training data 128. Training sets may be drawn from diverse sets of data such as, as non-limiting examples, novels, blog posts, articles, emails, user profile 108, and the like. In some embodiments, training sets may include a variety of subject matters, such as, as nonlimiting examples, oil and gas documents, entity documents, business documents, inventory documentation, emails, user communications, advertising documents, newspaper articles, and the like. In some embodiments, training sets of LLM 132 may include a plurality of user profiles 108. In some embodiments, training sets of LLM 132 may include information from one or more public or private databases. As a non-limiting example, training sets may include databases associated with an entity. In some embodiments, training sets may include portions of documents associated with the user profiles 108 correlated to examples of a first set of inquiries 116. In an embodiment, LLM 132 may include one or more architectures for based on the task requirements of LLM 132. Common architectures may include GPT (Generative Pretrained Transformer), BERT (Bidirectional Encoder Representations from Transformers), T5 (Text-To-Text Transfer Transformer), etc. The architecture choice depends on whether you need generative, contextual, or other specific capabilities.

With continued reference to FIG. 1, in some embodiments, LLM 132 may be generally trained. For the purposes of this disclosure, "generally trained" means that LLM 132 is trained on a general training set comprising a variety of subject matters, data sets, and fields. In some embodiments, LLM 132 may be initially generally trained. In some embodiments, for the purposes of this disclosure, LLM 132 may be specifically trained. For the purposes of this disclosure, "specifically trained" means that LLM 132 is trained on a specific training set, wherein the specific training set includes data including specific correlations for LLM 132 to learn. As a non-limiting example, LLM 132 may be generally trained on a general training set, then specifically trained on a specific training set. As a non-limiting example, specific training set may include examples of comprehensive reports. As a non-limiting example, specific training set may include scholastic works. As a non-limiting example, specific training set may include information from a database. As a non-limiting example, specific training set may include text related to the users such as user specific data and contextual data extracted from the user specific data correlated to examples of an inquiry machine learning model 124. In an embodiment, training the inquiry machine learning model 124 may include setting the parameters of the model (weights and biases) either randomly or using a pretrained model. Generally training the inquiry machine learning model 124 on a large corpus of text data can provide a starting point for fine-tuning on the specific task. The model may learn by adjusting its parameters during the training process to minimize a defined loss function, which measures the difference between predicted outputs and ground truth. Once the model has been generally trained, The model may then be specifically trained to fine-tune the pretrained model on task-specific data to adapt it to the target task. Fine-tuning involves training the model with user-specific training data, adjusting the model's weights to optimize performance for the particular task. In some cases, this may include optimizing the model's performance by fine-tuning hyperparameters such as learning rate, batch size, and regularization. Hyperparameter tuning helps in achieving the best performance and convergence during training.

With continued reference to FIG. 1, LLM 132, in some embodiments, may include Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. LLM 132 may include a text prediction based algorithm configured to receive an article and apply a probability distribution to the words already typed in a sentence to work out the most likely word to come next in augmented articles. For example, if the words already typed are "Nice to meet", then it is highly likely that the word "you" will come next. LLM 132 may output such predictions by ranking words by likelihood or a prompt parameter. For the example given above, the LLM 132 may score "you" as the most likely, "your" as the next most likely, "his" or "her" next, and the like. LLM 132 may include an encoder component and a decoder component.

Still referring to FIG. 1, LLM 132 may include a transformer architecture. In some embodiments, encoder component of LLM 132 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM 132 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, an attention mechanism may represent an improvement over a limitation of the Encoder-Decoder model. The encoder-decider model encodes the input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, LLM 132 may predict the next word by searching for a set of position in a source sentence where the most relevant information is concentrated. LLM 132 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, an attention mechanism may include generalized attention self-attention, multi-head attention, additive attention, global attention, and the like. In generalized attention, when a sequence of words or an image is fed to LLM 132, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, LLM 132 may pick up particular parts at different positions in the input sequence and over time compute an initial composition of the output sequence. In multi-head attention, LLM 132 may include a transformer model of an attention mechanism. Attention mechanisms, as described above, may provide context for any position in the input sequence. For example, if the input data is a natural language sentence, the transformer does not have to process one word at a time. In multi-head attention, computations by LLM 132 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), LLM 132 may make use of attention alignment scores based on a number of factors. These alignment scores may be calculated at different points in a neural network. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, LLM 132 may either attend to all source words or predict the target sentence, thereby attending to a smaller subset of words.

With continued reference to FIG. 1, multi-headed attention in encoder may apply a specific attention mechanism called self-attention. Self-attention allows the models to associate each word in the input, to other words. So, as a non-limiting example, the LLM 132 may learn to associate the word "you", with "how" and "are". It's also possible that LLM 132 learns that words structured in this pattern are typically a question and to respond appropriately. In some embodiments, to achieve self-attention, input may be fed into three distinct fully connected layers to create query, key, and value vectors. The query, key, and value vectors maybe fed through a linear layer; then, the query and key vectors may be multiplies using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With continued reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am", decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

With continued reference to FIG. 1, decoder may take this output and add it to the decoder inputs. Decoder may continue decoding until a token is predicted. Decoder may stop decoding once it predicts an end token.

With continued reference to FIG. 1, in some embodiment, decoder may be stacked N layers high, with each layer taking in inputs from the encoder and layers before it. Stacking layers may allow LLM 132 to learn to extract and focus on different combinations of attention from its attention heads.

With continued reference to FIG. 1, LLM 132 may receive an input. Input may include a string of one or more characters. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. Query may include, for example a question asking for a status update regarding a to-do list. In some embodiments, input may include a set of background data 116 associated with the user profile 108.

With continued reference to FIG. 1, LLM 132 may generate an output. In some embodiments, LLM 132 may include multiple sets of transformer architecture as described above. Output may include a textual output. A "textual output," for the purposes of this disclosure is an output comprising a string of one or more characters. Textual output may include, for example, a comprehensive report. In some embodiments, textual output may include a phrase or sentence identifying the status of a user query. In some embodiments, textual output may include a sentence or plurality of sentences describing a response to a user query. As a non-limiting examples, this may include, restrictions, timing, advice, dangers, benefits, and the like.

With continued reference to FIG. 1, machine learning plays a crucial role in enhancing the function of software for generating an inquiry machine learning model 124. This may include identifying patterns of within the user profile 108 that lead to changes in the capabilities and type of the inquiry machine learning model 124. By analyzing vast amounts of data related to biological data, machine learning algorithms can identify patterns, correlations, and dependencies that contribute to a generating the inquiry machine learning model 124. These algorithms can extract valuable insights from various sources, including text, document, audio, and other multimodal data associated with the user profile 108. By applying machine learning techniques, the software can generate the inquiry machine learning model 124 extremely accurately. Machine learning models may enable the software to learn from past collaborative experiences of the entities and iteratively improve its training data over time.

With continued reference to FIG. 1, processor 104 may be configured to update the training data of the inquiry machine learning model 124 using user inputs. A inquiry machine learning model 124 may use user input to update its training data, thereby improving its performance and accuracy. In embodiments, the inquiry machine learning model 124 may be iteratively updated using input and output results of the inquiry machine learning model 124. The inquiry machine learning model 124 may then be iteratively retrained using the updated machine-learning model. For instance, and without limitation, inquiry machine learning model 124 may be trained using a first training data from, for example, and without limitation, training data from a user input or database. The inquiry machine learning model 124 may then be updated by using previous inputs and outputs from the inquiry machine learning model 124 as second training data to then train a second machine learning model or a second iteration of the inquiry machine learning model 124 This process of updating the inquiry machine learning model 124 may be continuously done to create subsequent a second set of inquiries 120 which may be used to prompt the user to provide a second set of inquiry responses 156. The second set on inquiry responses may be used as training data for specifically training the inquiry machine-learning model 124. The additional training data provided by second set of inquiries 120 may be used to improve the speed and accuracy of the inquiry machine learning model 124. When users interact with the software, their actions, preferences, and feedback provide valuable information that can be used to refine and enhance the model. This user input is collected and incorporated into the training data, allowing the machine learning model to learn from real-world interactions and adapt its predictions accordingly. By continually incorporating user input, the model becomes more responsive to user needs and preferences, capturing evolving trends and patterns. This iterative process of updating the training data with user input enables the machine learning model to deliver more personalized and relevant results, ultimately enhancing the overall user experience. The discussion within this paragraph may apply to both the inquiry machine learning model 124 and/or any other machine-learning model/classifier discussed herein.

Incorporating the user feedback may include updating the training data by removing or adding correlations of user data to a path or resources as indicated by the feedback. Any machine-learning model as described herein may have the training data updated based on such feedback or data gathered using a web crawler as described above. For example, correlations in training data may be based on outdated information wherein, a web crawler may update such correlations based on more recent resources and information.

With continued reference to FIG. 1, processor 104 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another value that represents an ideal output given the input the machine learning model originally received, permitting use in retraining, and adding to training data; in either case, classifier may be retrained with modified training data as described in further detail below. In some embodiments, training data of classifier may include user feedback.

With continued reference to FIG. 1, in some embodiments, an accuracy score may be calculated for classifier using user feedback. For the purposes of this disclosure, "accuracy score," is a numerical value concerning the accuracy of a machine-learning model. For example, the accuracy/quality of the outputted inquiry machine learning model 124 may be averaged to determine an accuracy score. In some embodiments, an accuracy score may be determined for pairing of entities. Accuracy score or another score as described above may indicate a degree of retraining needed for a machine-learning model such as a classifier; processor 104 may perform a larger number of retraining cycles for a higher number (or lower number, depending on a numerical interpretation used), and/or may collect more training data for such retraining. The discussion within this paragraph and the paragraphs preceding this paragraph may apply to both the inquiry machine learning model 124 and/or any other machine-learning model/classifier mentioned herein.

With continued reference to FIG. 1, in one or more embodiments, processor 104 may implement one or more aspects of "generative artificial intelligence (AI)," a type of AI that uses machine learning algorithms to create, establish, or otherwise generate data such as, without limitation, user score or comprehensive report and/or the like in any data structure as described herein (e.g., text, image, video, audio, among others) that is similar to one or more provided training examples. In an embodiment, machine learning module described herein may generate one or more generative machine learning models that are trained on one or more set of event training data and/or report training data. One or more generative machine learning models May be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, "generative models" refers to statistical models of the joint probability distribution P(X, Y) on a given observable variable x, representing features or data that can be directly measured or observed (e.g. user profile 108 and contextual data) and target variable y, representing the outcomes or labels that one or more generative models aims to predict or generate (e.g., an inquiry machine learning model 124). In some cases, generative models may rely on Bayes theorem to find joint probability; for instance, and without limitation, Naïve Bayes classifiers may be employed by processor 104 to categorize input data such as, without limitation the contextual data and the user profile 108 into the first set of inquiries 116 and/or second set of inquiries 120.

In a non-limiting example, and still referring to FIG. 1, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)ΠiP(Xi|Y), wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of a comprehensive reports and/or a user scores based on inputs as described herein, wherein the models may be trained using training data containing a plurality of features, and/or the like as input correlated to a plurality of labeled classes.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 2.

With continued reference to FIG. 1, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 2 to distinguish between different categories, or states e.g., TRUE vs. FALSE within the context of generated data such as, without limitations, a comprehensive report and/or a user score, and/or the like. In some cases, processor 104 may implement one or more classification algorithms such as, without limitation, Support Vector Machines (SVM), Logistic Regression, Decision Trees, and/or the like to define decision boundaries.

With continued reference to FIG. 1, processor 104 is configured to receive a first set of inquiry responses 136 and/or second set of inquiry responses 156 as a function of the first set of inquiries 116 and/or second set of inquiries 120. As used in the current disclosure, a "inquiry response" is a response to the inquiry. A first set of inquiry responses 136 and/or second set of inquiry responses 156 may be generated as a function of the first set of inquiries 116. A first set of inquiry responses 136 may provide additional context or information regarding the user profile 108. The first set of inquiry responses 136 may describe in further detail any symptoms, medical tests, lifestyle factors, and the like of the user. An inquiry response 136 may be multimodal in nature. This may include images, videos, text, audio, and the like. A first set of inquiry responses 136 may include a recording of the performance of one or more actions by the user as instructed by the first set of inquiries 116. This may include tasks such as performance of medical tests, submission of additional medical imaging tests, and the like. A user's submission of the first set of inquiry responses 136 may be recorded using at least a sensor, as mentioned herein above. The sensor may include an audiovisual capture device. In a non-limiting example, a first set of inquiries 116 may ask a user to demonstrate their range of motion in one or more of their extremities. A possible inquiry response 136 to the user's inquiry may be a submission of a video with the user demonstrating their range of motion in their extremities. Alternatively, an appropriate submission may additionally text describing the range of motion of the user. The first set of inquiry responses 136 may be processed through the lens of the contextual data is used to provide context to the user profile 108. This is done with the goal of providing more tailored and accurate outputs to the user within the context of the user profile 108.

With continued reference to FIG. 1, processor 104 is configured to generate a diagnostic report 140 as a function of the first set of inquiries 116 and the first set of inquiry responses 136. As used in the current disclosure, a "diagnostic report" is a document that contains a summary of the findings associated with the user's health. A diagnostic report 140 may contain information about the user's medical history, including past and current medical conditions, surgeries, allergies, vaccinations, family medical history, and lifestyle factors. A diagnostic report 140 may additionally include documentation of the user's reported symptoms, including their onset, duration, frequency, intensity, aggravating or alleviating factors, and any other relevant details. In some cases, a diagnostic report 140 may include information about any observations obtained through an examination by apparatus 100. This may include vital signs (blood pressure, heart rate, temperature), palpation, auscultation, inspection, and other clinical assessments. In some cases, this may include determinations made from physical tests performed by the user as observed by apparatus 100. In additional embodiments, diagnostic report 140 may include results of various diagnostic laboratory tests, such as blood tests, urine tests, genetic testing, etc., providing information about the user's physiological and biochemical status. This can include values for blood glucose, lipid profiles, complete blood counts, etc. Additionally, a diagnostic report 140 may include the results of imaging tests such as X-rays, CT scans, MRIs, ultrasounds, mammograms, or other radiological studies that provide visual information about the internal structures of the body to aid in diagnosis. Additionally, a diagnostic report 140 may include results from tissue or cell analyses obtained through biopsies, surgeries, or other procedures, providing insights into the cellular or tissue-level characteristics for diagnosis (e.g., cancer diagnosis, infectious diseases). A diagnostic report 140 may provide the user with a diagnostic timeline. A diagnostic timeline may be a chronological listing of all events associated with the user ailments. A diagnostic timeline may include a timeline of the previous treatments, tests, diagnosis, prognosis, disease progression, and the like of the user.

With continued reference to FIG. 1, a diagnostic report 140 may contain diagnostic data. As used in the current disclosure, "diagnostic data" is data associated with the diagnosis of a user's medical condition or health issue. Processor 104 may generate diagnostic data as a function of the collected and analyzed data from the user profile 108, the first set of inquiries 116, and the first set of inquiry responses 136. Diagnostic data may identify the condition of or name of the disease the user is suffering from based on known conditions/symptoms of the user. In a non-limiting example, a user who is presenting chest pain, coughing up blood, a history of chronic smoking, dysphagia, and Shortness of Breath may be diagnosed with lung cancer after processor 104 evaluates medical images associated with the user. Processor 104 may identify and extract essential features or attributes from the user profile 108 to generate diagnostic data. Features may include specific symptoms, test results, demographic information, or other relevant data points. Feature extraction may involve identifying and transforming the symptom-related information from raw data into structured, quantifiable features that can be used by processor 104. Identification of the relevant features from the user profile 108 is a fundamental step in the process of generating diagnostic data. It may involves selecting and transforming relevant information (features) from the raw data that is informative and suitable for use in predictive modeling, pattern recognition, or any other data-driven task. In some cases, processor 104 may be configured to leverage specialized medical ontologies and dictionaries, such as SNOMED CT (Systematized Nomenclature of Medicine—Clinical Terms) or UMLS (Unified Medical Language System), to map symptom-related terms to standardized medical concepts. This ensures consistency and interoperability in the extracted features. Processor 104 may analyzed the context in which symptoms are mentioned within the user profile 108 to extract semantic meaning. In a non-limiting example, this may include understanding negation (e.g., "not experiencing pain"), co-occurrences, and modifiers (e.g., "severe headache") is essential for accurate feature extraction. Feature extraction may additionally include quantifying the frequency and severity of each symptom by analyzing descriptors like "frequent," "occasional," "mild," "moderate," or "severe." Assigning numerical values or ordinal scales to represent these aspects allows for quantitative analysis. Additionally, processor 104 may extract temporal information related to symptoms, such as the duration of symptoms (e.g., "persisting for 2 weeks"), onset dates, and any patterns of symptom occurrence (e.g., "worsens in the morning"). Processor 104 then may group related symptoms into clusters or categories based on their characteristics and related medical concepts. Clustering helps reduce the dimensionality of the feature space and organize symptoms for analysis. In a non-limiting example, the user profile 108 the user has cough, fever, chest pain. Processor 104 may associate this cluster with lower respiratory symptoms. Processor 104 may then generate diagnostic data based on the known diagnoses associated with this cluster (Asthma, Pneumonia), the system suggests further diagnostic tests or evaluations to narrow down the diagnosis.

With continued reference to FIG. 1, a diagnostic report 140 may contain a treatment plan. As used in current disclosure, a "treatment plan" is a structured, comprehensive, and individualized document outlining the course of action to be taken to manage a medical condition or health issue effectively. Processor 104 may develop a treatment plan based on a thorough assessment of the patient's diagnosis, medical history, symptoms, test results, and other relevant information. The primary goal of a treatment plan is to provide a roadmap for achieving optimal health outcomes, enhancing the quality of life, and addressing the specific needs and goals of the patient. A treatment plan may include a description of the proposed treatments, therapies, and interventions to address the diagnosis. This can encompass medications, surgeries, physical therapy, psychotherapy, dietary modifications, lifestyle changes, assistive devices, and more. In some embodiments, this may include specific details about prescribed medications, including names, dosages, frequencies, instructions for administration, potential side effects, and precautions. Processor 104 may generate a treatment plan as a function of the diagnostic data. This may identifying known treatments for a given diagnosis and selecting the appropriate treatment of the particular user based upon the severity, age, sex, size, and the like of the user. In a non-limiting example, processor 104 may generate a treatment plan for a user who has been diagnosed with lung cancer. Processor 104 may identify the type, stage, and severity of the lung cancer based on imaging studies, biopsies, and other diagnostic tests. Processor 104 may then identify a clear, measurable goal for the treatment, such as tumor shrinkage, symptom relief, improved quality of life, or extended survival. Processor 104 may then identify known treatments for the lung cancer such as a surgery, radiation therapy, chemotherapy, targeted therapy, immunotherapy, or a combination of these. Processor 104 may then select the ideal treatment to achieve the defined goal based on a combination of demographic factors (i.e. age, sex, weight, overall health, and the like) and user preference. In some cases, a treatment plan may include a schedule for monitoring the patient's progress, follow-up appointments, tests, and assessments to evaluate the treatment's effectiveness. This may also include criteria for adjusting the treatment plan based on the observed outcomes.

With continued reference to FIG. 1, processor 104 may generate diagnostic report 140 using a diagnostic machine-learning model 144. As used in the current disclosure, a "diagnostic machine-learning model" is a machine-learning model that is configured to generate diagnostic report 140. The diagnostic machine-learning model 144 may be consistent with the machine-learning model described below in FIG. 2. Inputs to the diagnostic machine-learning model 144 may include user profile 108, biological data 112, the first set of inquiries 116, second set of inquiries 120, confidence scores 152, non-user specific training data 128, contextual data, first set of inquiry responses 136, examples of diagnostic reports 140, examples of diagnostic data, examples of treatment plans, and the like. Outputs to the diagnostic machine-learning model 144 may include diagnostic report 140 tailored to user profile 108. Additional outputs to the diagnostic machine learning model may include treatment plans and diagnostic data. Diagnostic training data may include a plurality of data entries containing a plurality of inputs that are correlated to a plurality of outputs for training a processor by a machine-learning process. In an embodiment, diagnostic training data may include the first set of inquiries 116 and the first set of inquiry responses 136 correlated to examples of diagnostic reports 140. Diagnostic training data may be received from database. Diagnostic training data may contain information about user profile 108, biological data 112, the first set of inquiries 116, second set of inquiries 120, confidence scores 152 non-user specific training data 128, contextual data, first set of inquiry responses 136, examples of diagnostic reports 140, examples of diagnostic data, examples of treatment plans, examples of diagnostic report 140, and the like. In an embodiment, diagnostic training data may be iteratively updated as a function of the input and output results of past diagnostic machine-learning model 144 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, generate a confidence score 152 for the diagnostic report 140. As used in the current disclosure, a "confidence score" is a score that reflects the probability that a given diagnostic report 140 is accurate. A confidence score 152 may reflect the level of certainty or reliability associated with the diagnostic report 140, diagnostic data, and/or treatment score. This score may indicate the confidence processor 104 has in the accuracy of the diagnosis. A confidence score 152 may be generated by a confidence machine learning model as a described herein below. Processor 104 may utilize the confidence machine learning model to predict the data contained in the diagnostic report 140. Processor 104 may normalize the confidence scores 152 to ensure they fall within a consistent range (e.g., 0-1, 0-10, 0-100, and the like) for ease of interpretation. Processor 104 may incorporate uncertainty measures based on the model's prediction confidence, such as variance, entropy, or Bayesian probabilities. Higher uncertainty might indicate a lower confidence score 152. Processor 104 may adjust confidence score 152 based on known clinical factors. For instance, if a critical symptom aligns strongly with a particular diagnosis, it could boost the confidence for that diagnosis. A confidence score 152 may be reflected using an alphanumeric score or other linguistic identifiers. A linguistic identifier may include identifiers such as "Highly Confident," "Moderately Confident," "Moderately Unconfident, " "Highly Unconfident," "No Response Available," "Query out of scope," and the like.

With continued reference to FIG. 1, processor 104 may compare the confidence score 152 to a confidence threshold. As used in the current disclosure, a "confidence threshold" is a predefined level of confidence or probability that is used to make decisions or take actions based on the output of a machine learning model. A confidence score 152 may serve as a cutoff point or boundary beyond which the model's predictions or classifications are considered reliable and actionable. In an embodiment, when the confidence score 152 surpasses the defined threshold, the model's output is accepted as accurate and trustworthy. Conversely, if the confidence score 152 falls below this threshold, the prediction may be deemed less reliable, and further review, manual intervention, or an alternative approach may be warranted. In an embodiment, processor 104 may generate a second set of inquiries 120 if the confidence score 152 fails to reach the confidence threshold. Processor 104 may then be configured to receive the second set of inquiry responses 156 as a function of the second set of inquiries 120. Both the second set of inquiries 120 and the second set of inquiry responses 156 may be used as training data within the diagnostic machine-learning model 144. This may be done with a goal of refining the inputs into the diagnostic machine-learning model 144 to further refine the diagnostic report. In a non-limiting example, a confidence threshold could be set at 0.7. If the diagnostic machine-learning model 144 predicts a particular diagnosis with a confidence score 152 of 0.8, it exceeds the threshold, indicating high confidence. Conversely, if the model predicts a diagnosis with a confidence score 152 of 0.6, it falls below the threshold, suggesting lower confidence. As a result of the confidence score 152 falling below the threshold the a second set of inquiries 120 and the second set of inquiry responses 156 may be imputed into the diagnostic machine-learning model 144 with the goal of improving the output of the diagnostic report 140, diagnostic data, and treatment plans.

With continued reference to FIG. 1, processor 104 may generate confidence score 152 using a confidence machine-learning model. As used in the current disclosure, a "confidence machine-learning model" is a machine-learning model that is configured to generate confidence score 152. A confidence machine-learning model may be consistent with the machine-learning model described below in FIG. 2. Inputs to the confidence machine-learning model may include user profile 108, biological data 112, the first set of inquiries 116, second set of inquiries 120, confidence scores 152, non-user specific training data 128, contextual data, first set of inquiry responses 136, diagnostic reports 140, diagnostic data, treatment plans, examples of confidence scores 152, and the like. Outputs to the confidence machine-learning model may include confidence score 152 tailored to the diagnostic report 140. Confidence training data may include a plurality of data entries containing a plurality of inputs that are correlated to a plurality of outputs for training a processor by a machine-learning process. The confidence machine learning model may be trained using confidence training data. The confidence training data would include both the symptoms from the user profile 108 and the corresponding accurate diagnoses associated with the diagnostic report 140, along with a confidence weight for each diagnosis. In an embodiment, confidence training data may include a plurality of diagnostic report 140 correlated to examples of confidence scores 152. confidence training data may be received from database 300. confidence training data may contain information about user profile 108, biological data 112, the first set of inquiries 116, second set of inquiries 120, confidence scores 152, non-user specific training data 128, contextual data, first set of inquiry responses 136, diagnostic reports 140, diagnostic data, treatment plans, examples of confidence scores 152, and the like. In an embodiment, confidence training data may be iteratively updated as a function of the input and output results of past confidence machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Still referring to FIG. 1, processor 104 may be configured to display a diagnostic report 140 using a display device 148. As used in the current disclosure, a "display device" is a device that is used to display a plurality of data and other digital content. A display device 148 may include a user interface. A "user interface," as used herein, is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

With continued reference to FIG. 1, apparatus 100 may perform or implement one or more aspects of a cryptographic system to encrypt a diagnostic report 140. In one embodiment, a cryptographic system is a system that converts data from a first form, known as "plaintext," which is intelligible when viewed in its intended format, into a second form, known as "ciphertext," which is not intelligible when viewed in the same way. Ciphertext may be unintelligible in any format unless first converted back to plaintext. In one embodiment, a process of converting plaintext into ciphertext is known as "encryption." Encryption process may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

With continued reference to FIG. 1, in embodiments of cryptographic systems that are "asymmetric," either encryption or decryption key cannot be readily deduced without additional secret knowledge, even given the possession of a corresponding decryption or encryption key, respectively; a common example is a "public key cryptographic system," in which possession of the encryption key does not make it practically feasible to deduce the decryption key, so that the encryption key may safely be made available to the public. An example of a public key cryptographic system is RSA, in which an encryption key involves the use of numbers that are products of very large prime numbers, but a decryption key involves the use of those very large prime numbers, such that deducing the decryption key from the encryption key requires the practically infeasible task of computing the prime factors of a number which is the product of two very large prime numbers. Another example is elliptic curve cryptography, which relies on the fact that given two points P and Q on an elliptic curve over a finite field, and a definition for addition where A+B=−R, the point where a line connecting point A and point B intersects the elliptic curve, where "0," the identity, is a point at infinity in a projective plane containing the elliptic curve, finding a number k such that adding P to itself k times results in Q is computationally impractical, given correctly selected elliptic curve, finite field, and P and Q.

With continued reference to FIG. 1, in some embodiments, systems and methods described herein produce cryptographic hashes, also referred to by the equivalent shorthand term "hashes." A cryptographic hash, as used herein, is a mathematical representation of a lot of data, such as files or blocks in a block chain as described in further detail below; the mathematical representation is produced by a lossy "one-way" algorithm known as a "hashing algorithm." Hashing algorithm may be a repeatable process; that is, identical lots of data may produce identical hashes each time they are subjected to a particular hashing algorithm. Because hashing algorithm is a one-way function, it may be impossible to reconstruct a lot of data from a hash produced from the lot of data using the hashing algorithm. In the case of some hashing algorithms, reconstructing the full lot of data from the corresponding hash using a partial set of data from the full lot of data may be possible only by repeatedly guessing at the remaining data and repeating the hashing algorithm; it is thus computationally difficult if not infeasible for a single computer to produce the lot of data, as the statistical likelihood of correctly guessing the missing data may be extremely low. However, the statistical likelihood of a computer of a set of computers simultaneously attempting to guess the missing data within a useful timeframe may be higher, permitting mining protocols as described in further detail below.

With continued reference to FIG. 1, in an embodiment, hashing algorithm may demonstrate an "avalanche effect," whereby even extremely small changes to lot of data produce drastically different hashes. This may thwart attempts to avoid the computational work necessary to recreate a hash by simply inserting a fraudulent datum in data lot, enabling the use of hashing algorithms for "tamper-proofing" data such as data contained in an immutable ledger as described in further detail below. This avalanche or "cascade" effect may be evinced by various hashing processes; persons skilled in the art, upon reading the entirety of this disclosure, will be aware of various suitable hashing algorithms for purposes described herein. Verification of a hash corresponding to a lot of data may be performed by running the lot of data through a hashing algorithm used to produce the hash. Such verification may be computationally expensive, albeit feasible, potentially adding up to significant processing delays where repeated hashing, or hashing of large quantities of data, is required, for instance as described in further detail below. Examples of hashing programs include, without limitation, SHA256, a NIST standard; further current and past hashing algorithms include Winternitz hashing algorithms, various generations of Secure Hash Algorithm (including "SHA-1," "SHA-2," and "SHA-3"), "Message Digest" family hashes such as "MD4," "MD5," "MD6," and "RIPEMD," Keccak, "BLAKE" hashes and progeny (e.g., "BLAKE2," "BLAKE-256," "BLAKE-512," and the like), Message Authentication Code ("MAC")-family hash functions such as PMAC, OMAC, VMAC, HMAC, and UMAC, Poly1305-AES, Elliptic Curve Only Hash ("ECOH") and similar hash functions, Fast-Syndrome-based (FSB) hash functions, GOST hash functions, the Grøstl hash function, the HAS-160 hash function, the JH hash function, the RadioGatun hash function, the Skein hash function, the Streebog hash function, the SWIFFT hash function, the Tiger hash function, the Whirlpool hash function, or any hash function that satisfies, at the time of implementation, the requirements that a cryptographic hash be deterministic, infeasible to reverse-hash, infeasible to find collisions, and have the property that small changes to an original message to be hashed will change the resulting hash so extensively that the original hash and the new hash appear uncorrelated to each other. A degree of security of a hash function in practice may depend both on the hash function itself and on characteristics of the message and/or digest used in the hash function. For example, where a message is random, for a hash function that fulfills collision-resistance requirements, a brute-force or "birthday attack" may to detect collision may be on the order of $O(2^{n/2})$ for n output bits; thus, it may take on the order of $2^{256}$ operations to locate a collision in a 512 bit output "Dictionary" attacks on hashes likely to have been generated from a non-random original text can have a lower computational complexity, because the space of entries they are guessing is far smaller than the space containing all random permutations of bits. However, the space of possible messages may be augmented by increasing the length or potential length of a possible message, or by implementing a protocol whereby one or more randomly selected strings or sets of data are added to the message, rendering a dictionary attack significantly less effective.

Continuing to refer to FIG. 1, a "secure proof," as used in this disclosure, is a protocol whereby an output is generated that demonstrates possession of a secret, such as device-specific secret, without demonstrating the entirety of the device-specific secret; in other words, a secure proof by itself, is insufficient to reconstruct the entire device-specific secret, enabling the production of at least another secure proof using at least a device-specific secret. A secure proof may be referred to as a "proof of possession" or "proof of knowledge" of a secret. Where at least a device-specific secret is a plurality of secrets, such as a plurality of challenge-response pairs, a secure proof may include an output that reveals the entirety of one of the plurality of secrets, but not all of the plurality of secrets; for instance, secure proof may be a response contained in one challenge-response pair. In an embodiment, proof may not be secure; in other words, proof may include a one-time revelation of at least a device-specific secret, for instance as used in a single challenge-response exchange.

With continued reference to FIG. 1, secure proof may include a zero-knowledge proof, which may provide an output demonstrating possession of a secret while revealing none of the secret to a recipient of the output; zero-knowledge proof may be information-theoretically secure, meaning that an entity with infinite computing power would be unable to determine secret from output. Alternatively, zero-knowledge proof may be computationally secure, meaning that determination of secret from output is computationally infeasible, for instance to the same extent that determination of a private key from a public key in a public key cryptographic system is computationally infeasible. Zero-knowledge proof algorithms may generally include a set of two algorithms, a prover algorithm, or "P," which is used to prove computational integrity and/or possession of a secret, and a verifier algorithm, or "V" whereby a party may check the validity of P. Zero-knowledge proof may include an interactive zero-knowledge proof, wherein a party verifying the proof must directly interact with the proving party; for instance, the verifying and proving parties may be required to be online, or connected to the same network as each other, at the same time. Interactive zero-knowledge proof may include a "proof of knowledge" proof, such as a Schnorr algorithm for proof on knowledge of a discrete logarithm. in a Schnorr algorithm, a prover commits to a randomness r, generates a message based on r, and generates a message adding r to a challenge c multiplied by a discrete logarithm that the prover is able to calculate; verification is performed by the verifier who produced c by exponentiation, thus checking the validity of the discrete logarithm. Interactive zero-knowledge proofs may alternatively or additionally include sigma protocols. Persons skilled in the art, upon reviewing the entirety of this disclosure, will be aware of various alternative interactive zero-knowledge proofs that may be implemented consistently with this disclosure.

With continued reference to FIG. 1, alternatively, zero-knowledge proof may include a non-interactive zero-knowledge, proof, or a proof wherein neither party to the proof interacts with the other party to the proof; for instance, each of a party receiving the proof and a party providing the proof may receive a reference datum which the party providing the proof may modify or otherwise use to perform the proof. As a non-limiting example, zero-knowledge proof may include a succinct non-interactive arguments of knowledge (ZK-SNARKS) proof, wherein a "trusted setup" process creates proof and verification keys using secret (and subsequently discarded) information encoded using a public key cryptographic system, a prover runs a proving algorithm using the proving key and secret information available to the prover, and a verifier checks the proof using the verification key; public key cryptographic system may include RSA, elliptic curve cryptography, ElGamal, or any other suitable public key cryptographic system. Generation of trusted setup may be performed using a secure multiparty computation so that no one party has control of the totality of the secret information used in the trusted setup; as a result, if any one party generating the trusted setup is trustworthy, the secret information may be unrecoverable by malicious parties. As another non-limiting example, non-interactive zero-knowledge proof may include a Succinct Transparent Arguments of Knowledge (ZK-STARKS) zero-knowledge proof. In an embodiment, a ZK-STARKS proof includes a Merkle root of a Merkle tree representing evaluation of a secret computation at some number of points, which may be 1 billion points, plus Merkle branches representing evaluations at a set of randomly selected points of the number of points; verification may include determining that Merkle branches provided match the Merkle root, and that point verifications at those branches represent valid values, where validity is shown by demonstrating that all values belong to the same polynomial created by transforming the secret computation. In an embodiment, ZK-STARKS does not require a trusted setup.

With continued reference to FIG. 1, a zero-knowledge proof may include any other suitable zero-knowledge proof. Zero-knowledge proof may include, without limitation, bulletproofs. Zero-knowledge proof may include a homomorphic public-key cryptography (hPKC)-based proof. Zero-knowledge proof may include a discrete logarithmic problem (DLP) proof. Zero-knowledge proof may include a secure multi-party computation (MPC) proof. Zero-knowledge proof may include, without limitation, an incrementally verifiable computation (IVC). Zero-knowledge proof may include an interactive oracle proof (IOP). Zero-knowledge proof may include a proof based on the probabilistically checkable proof (PCP) theorem, including a linear PCP (LPCP) proof. Persons skilled in the art, upon reviewing the entirety of this disclosure, will be aware of various forms of zero-knowledge proofs that may be used, singly or in combination, consistently with this disclosure.

With continued reference to FIG. 1, in an embodiment, secure proof is implemented using a challenge-response protocol. In an embodiment, this may function as a one-time pad implementation; for instance, a manufacturer or other trusted party may record a series of outputs ("responses") produced by a device possessing secret information, given a series of corresponding inputs ("challenges"), and store them securely. In an embodiment, a challenge-response protocol may be combined with key generation. A single key may be used in one or more digital signatures as described in further detail below, such as signatures used to receive and/or transfer possession of crypto-currency assets; the key may be discarded for future use after a set period of time. In an embodiment, varied inputs include variations in local physical parameters, such as fluctuations in local electromagnetic fields, radiation, temperature, and the like, such that an almost limitless variety of private keys may be so generated. Secure proof may include encryption of a challenge to produce the response, indicating possession of a secret key. Encryption may be performed using a private key of a public key cryptographic system, or using a private key of a symmetric cryptographic system; for instance, trusted party may verify response by decrypting an encryption of challenge or of another datum using either a symmetric or public-key cryptographic system, verifying that a stored key matches the key used for encryption as a function of at least a device-specific secret. Keys may be generated by random variation in selection of prime numbers, for instance for the purposes of a cryptographic system such as RSA that relies prime factoring difficulty. Keys may be generated by randomized selection of parameters for a seed in a cryptographic system, such as elliptic curve cryptography, which is generated from a seed. Keys may be used to generate exponents for a cryptographic system such as Diffie-Helman or ElGamal that are based on the discrete logarithm problem.

With continued reference to FIG. 1, A "digital signature," as used herein, includes a secure proof of possession of a secret by a signing device, as performed on provided element of data, known as a "message." A message may include an encrypted mathematical representation of a file or other set of data using the private key of a public key cryptographic system. Secure proof may include any form of secure proof as described above, including without limitation encryption using a private key of a public key cryptographic system as described above. Signature may be verified using a verification datum suitable for verification of a secure proof; for instance, where secure proof is enacted by encrypting message using a private key of a public key cryptographic system, verification may include decrypting the encrypted message using the corresponding public key and comparing the decrypted representation to a purported match that was not encrypted; if the signature protocol is well-designed and implemented correctly, this means the ability to create the digital signature is equivalent to possession of the private decryption key and/or device-specific secret. Likewise, if a message making up a mathematical representation of file is well-designed and implemented correctly, any alteration of the file may result in a mismatch with the digital signature; the mathematical representation may be produced using an alteration-sensitive, reliably reproducible algorithm, such as a hashing algorithm as described above. A mathematical representation to which the signature may be compared may be included with signature, for verification purposes; in other embodiments, the algorithm used to produce the mathematical representation may be publicly available, permitting the easy reproduction of the mathematical representation corresponding to any file.

Still viewing FIG. 1, in some embodiments, digital signatures may be combined with or incorporated in digital certificates. In one embodiment, a digital certificate is a file that conveys information and links the conveyed information to a "certificate authority" that is the issuer of a public key in a public key cryptographic system. Certificate authority in some embodiments contains data conveying the certificate authority's authorization for the recipient to perform a task. The authorization may be the authorization to access a given datum. The authorization may be the authorization to access a given process. In some embodiments, the certificate may identify the certificate authority. The digital certificate may include a digital signature.

With continued reference to FIG. 1, in some embodiments, a third party such as a certificate authority (CA) is available to verify that the possessor of the private key is a particular entity; thus, if the certificate authority may be trusted, and the private key has not been stolen, the ability of an entity to produce a digital signature confirms the identity of the entity and links the file to the entity in a verifiable way. Digital signature may be incorporated in a digital certificate, which is a document authenticating the entity possessing the private key by authority of the issuing certificate authority and signed with a digital signature created with that private key and a mathematical representation of the remainder of the certificate. In other embodiments, digital signature is verified by comparing the digital signature to one known to have been created by the entity that purportedly signed the digital signature; for instance, if the public key that decrypts the known signature also decrypts the digital signature, the digital signature may be considered verified. Digital signature may also be used to verify that the file has not been altered since the formation of the digital signature.

Figure 2:
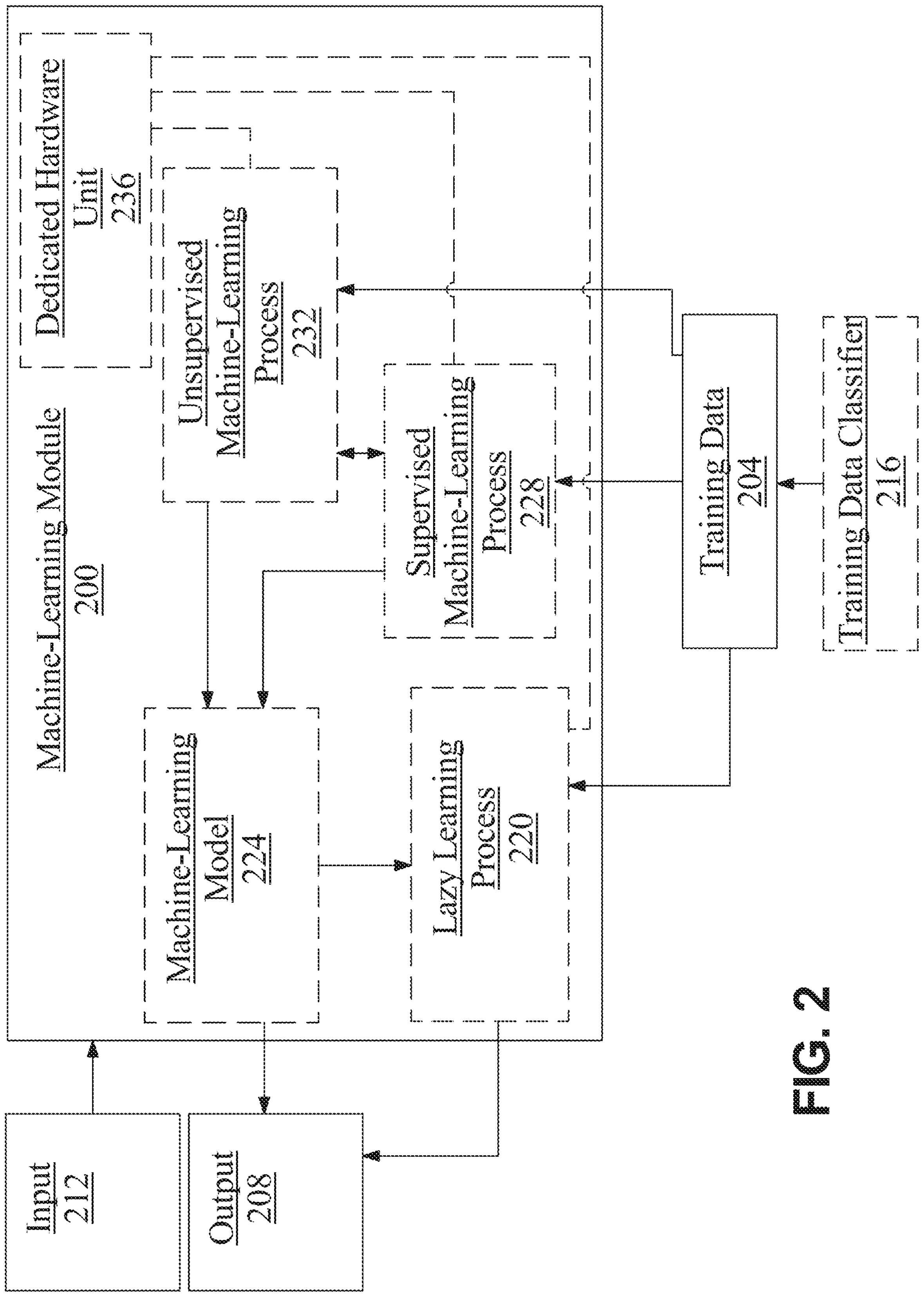
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, user profiles 108 as inputs correlated to a first set of inquiries 116 as outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements of biological data 112 to examples of diagnostic data.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include user profiles 108 as described above as inputs, a first set of user inquiries 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
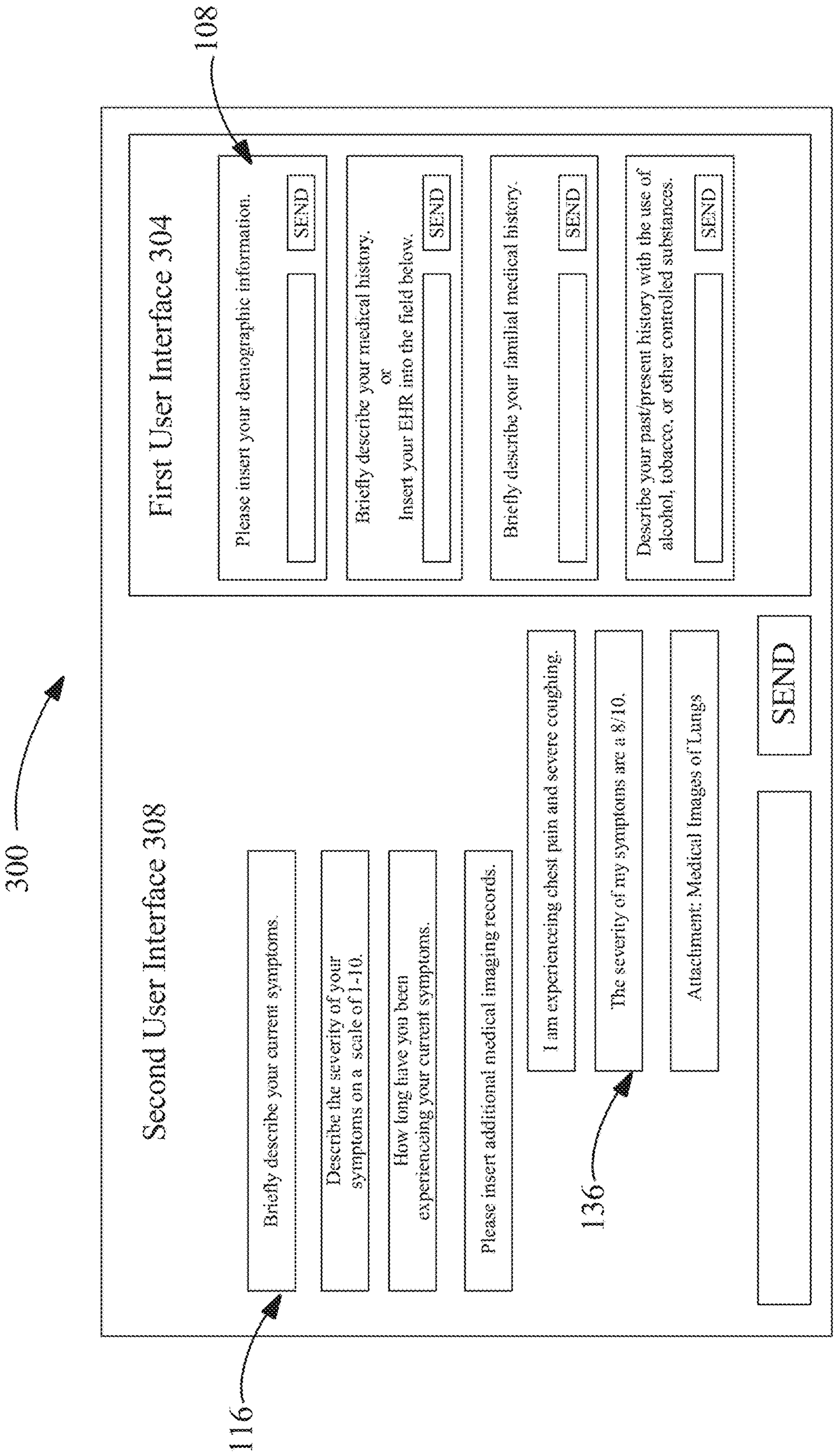
FIG. 3 is an illustration of an exemplary embodiment of a plurality of user interfaces.

Referring now to FIG. 3, an exemplary embodiment of a plurality of user interfaces. As used in the current disclosure, a "user interface" is the point of interaction between a user and a digital system or device. A user interface may include elements and mechanisms that enable users to interact with and control the system, application, or software in a visually understandable and intuitive manner. The primary goal of a user interface is to enhance user experience by presenting information in a clear, efficient, and aesthetically pleasing way. FIG. 3 depicts at least two distinct user interfaces, a first user interface 304 and a second user interface 308 respectively. The first user interface 304 may be configured to allow the user to submit information associated with the user profile 108 via one or more input fields. Input fields may include text boxes, dropdown menus, buttons, icons, and the like. The input fields of the first user interface 304 may allow the user to submit text, images, audio, documents, video, and the like. The first user interface 304 may allow the user to submit, adjust, or modify portions of the user profile 108, The second user interface 308 may take the form of a chatbot, as discussed in greater detail herein below, to submit the first set of inquiries 116 and/or the second set of inquiries 120 to the user. Additionally, the second user interface 308 may allow the user to respond to the first set of inquiries 116 and/or the second set of inquiries 120 using the first set of inquiry responses 136 and/or second set of inquiry responses 156. The user may submit the first set of inquiry responses 136 and/or second set of inquiry responses 156 using one or more input fields. In some cases, the second user interface 308 may be communicatively connected to at least a sensor. The sensor may be configured to allow the user to record video, audio, and the like as the first set of inquiry responses 136 and/or second set of inquiry responses 156. In an embodiment, a user may be connected via audio or video call to a medical professional through a user interface. Apparatus 100 may connect the user based on the results contained in the diagnostic report 140 or user profile 108.

Figure 4:
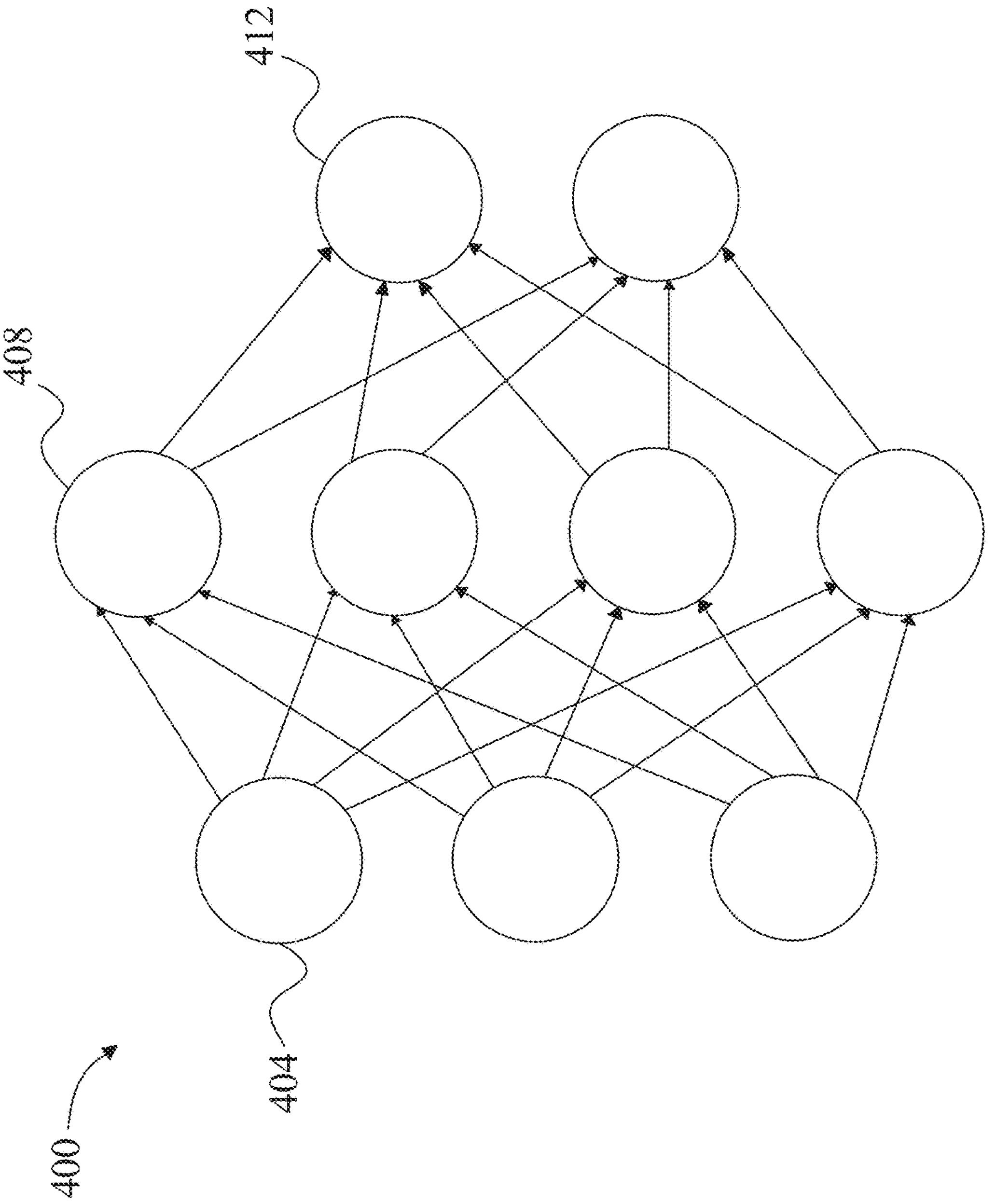
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
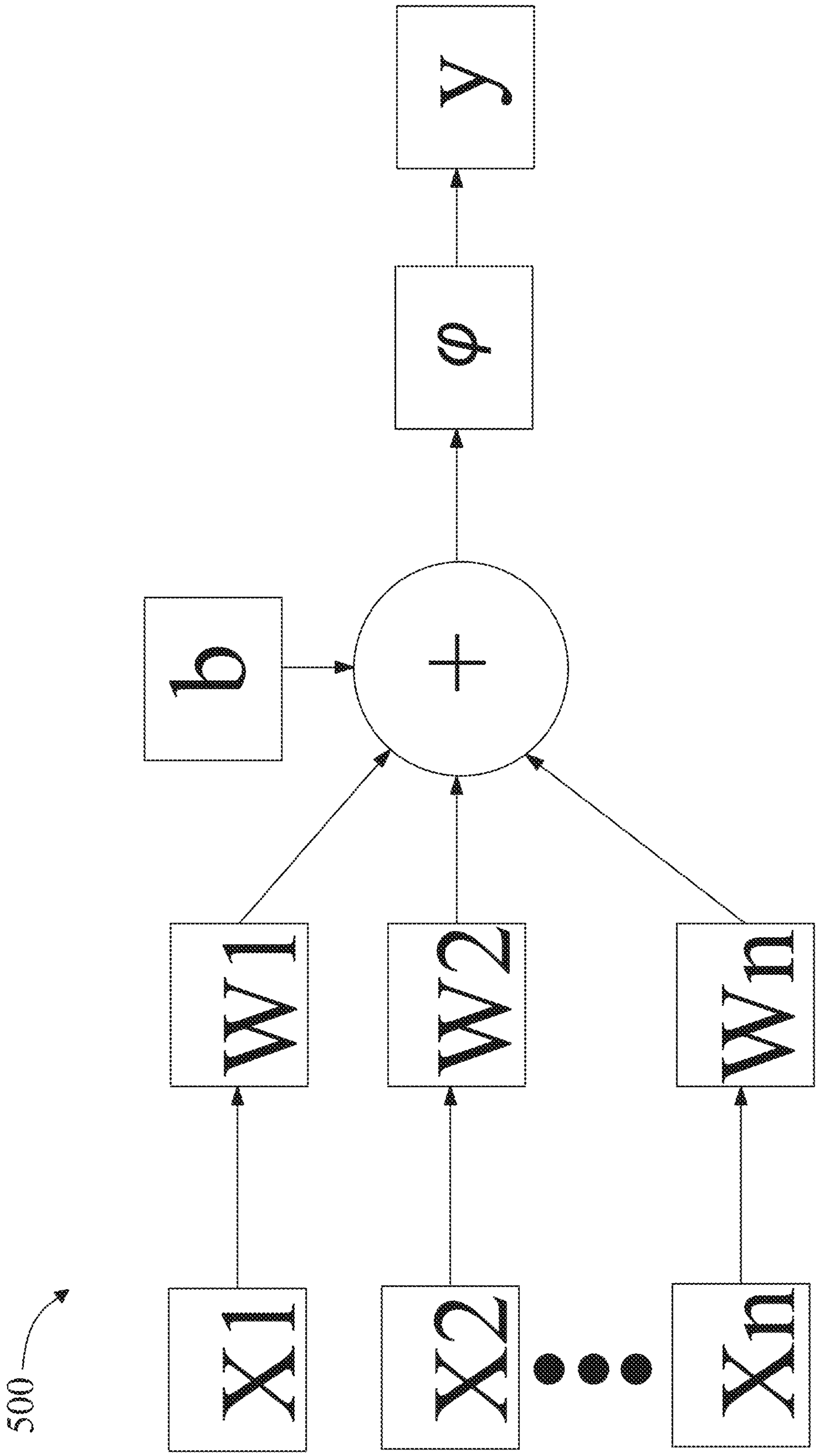
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
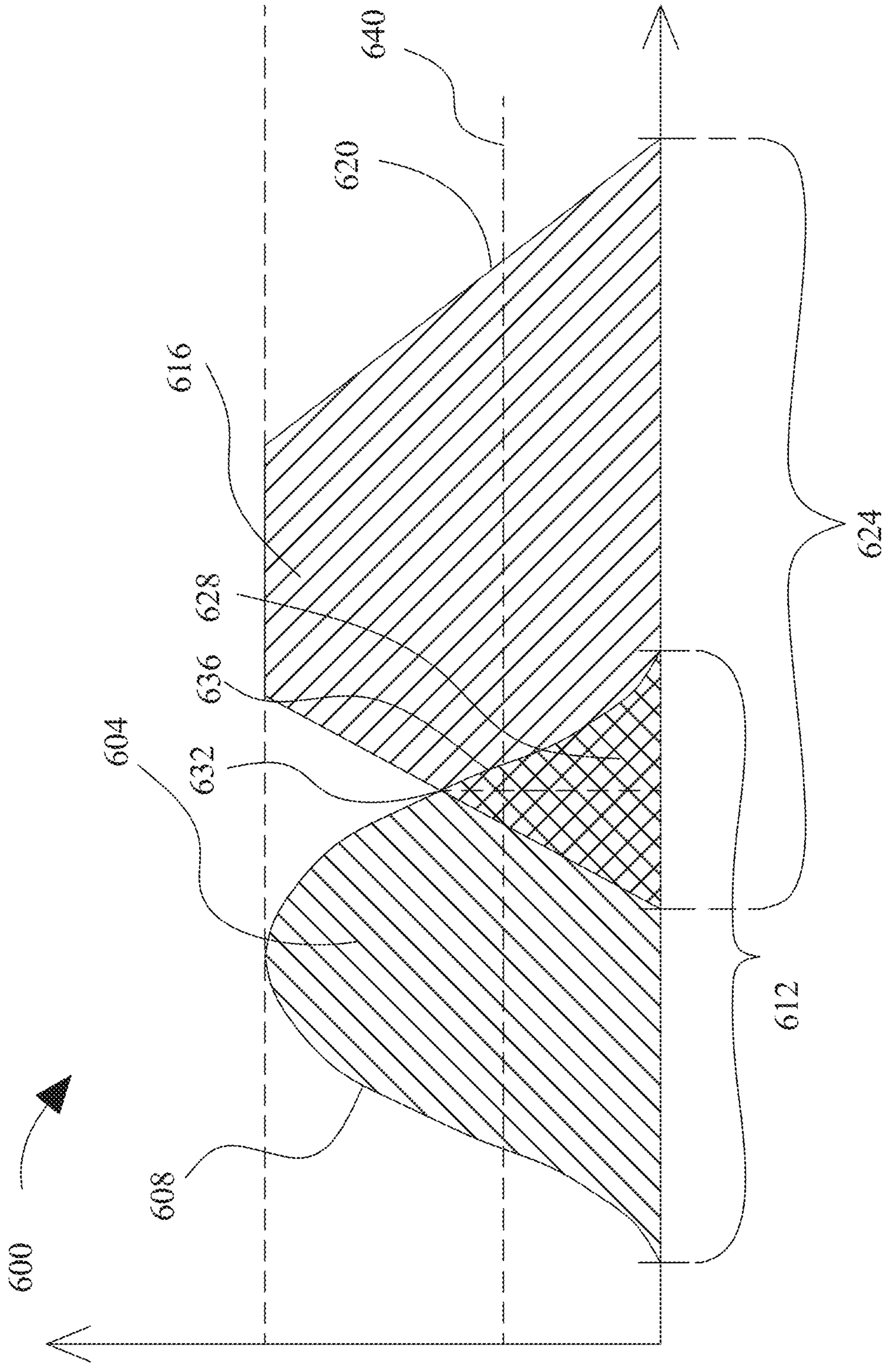
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent biological data 112 and diagnostic data from FIG. 1.

Alternatively or additionally, and still referring to FIG. 6, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input biological data 112 and diagnostic data. For instance, an acceptance variable may represent a first measurable value pertaining to the classification of biological data 112 to diagnostic data. Continuing the example, an output variable may represent diagnostic data associated with the user. In an embodiment, biological data 112 and/or diagnostic data may be represented by their own fuzzy set. In other embodiments, the classification of the data into diagnostic data may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any biological data 112 and diagnostic data. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the classification into one or more query categories may indicate a sufficient degree of overlap with fuzzy set representing biological data 112 and diagnostic data for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both biological data 112 and diagnostic data have fuzzy sets, diagnostic data may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
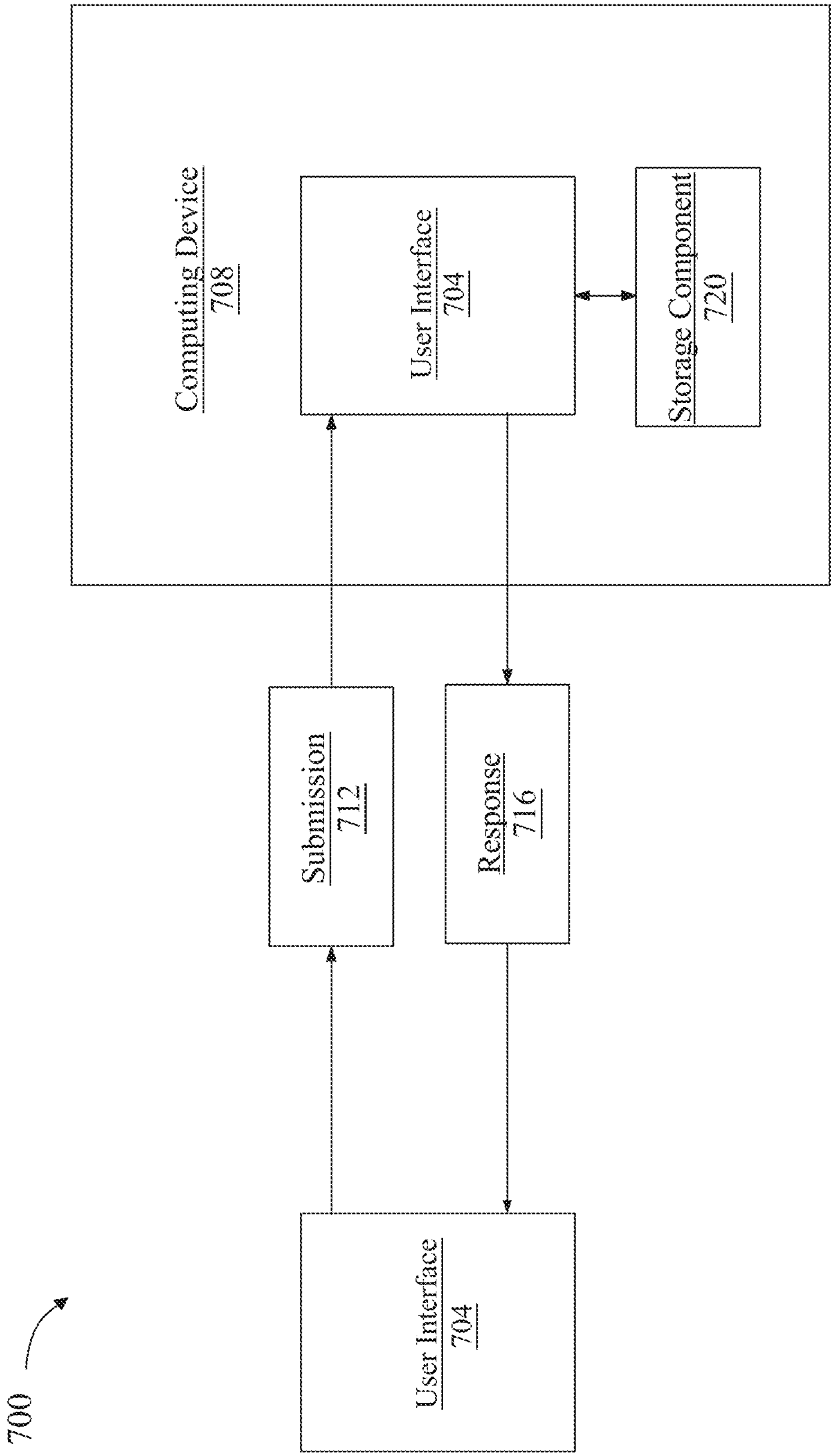
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both of submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more of keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 8:
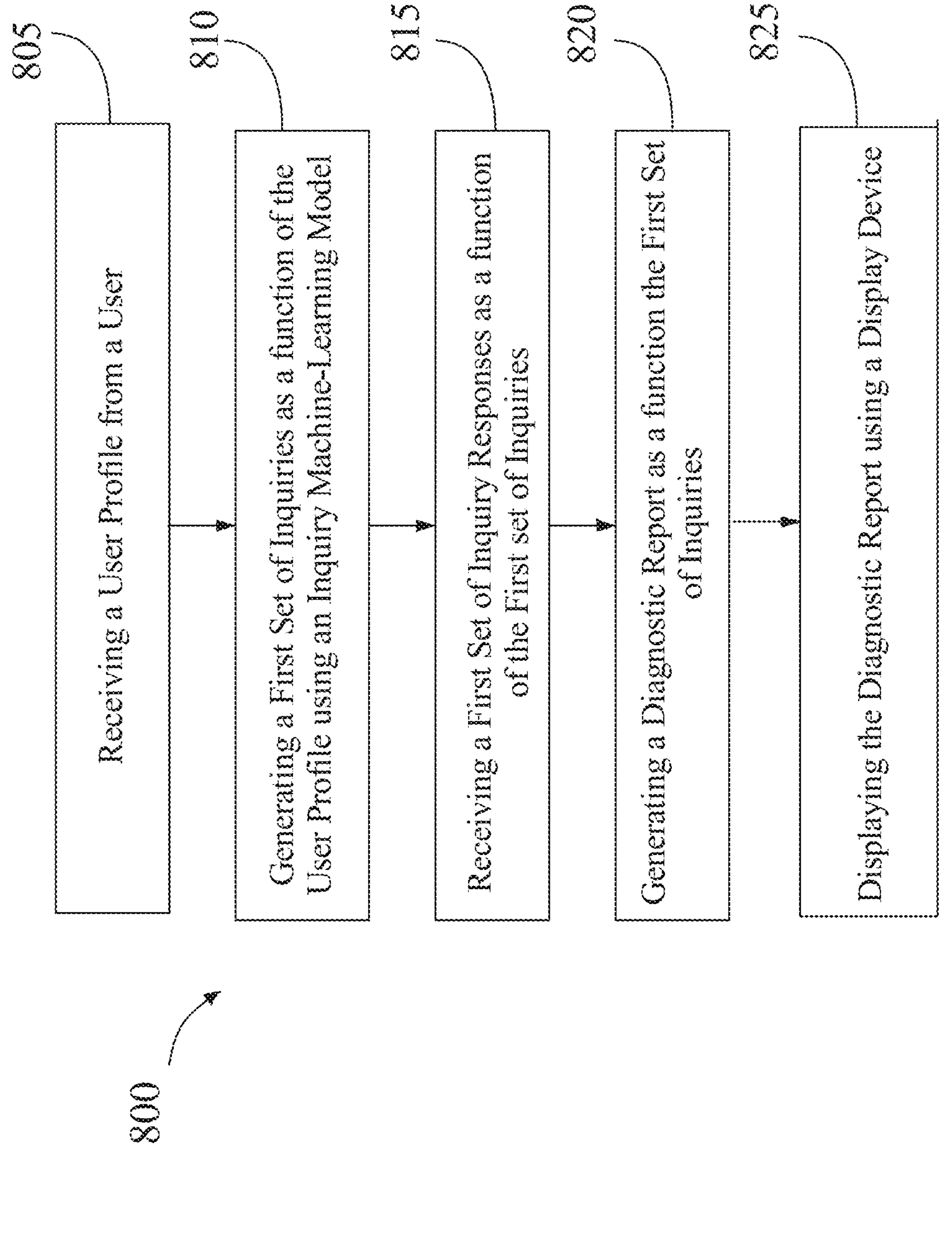
FIG. 8 is a flow diagram of an exemplary method for generating a diagnostic report.

Referring now to FIG. 8, a flow diagram of an exemplary method 800 for generating a diagnostic report is illustrated. At step 805, method 800 includes receiving, using at least a processor, a user profile from a user. This may be implemented as described and with reference to FIGS. 1-7. In an embodiment, the user profile may include a plurality of biological data associated with the user.

Still referring to FIG. 8, at step 810, method 800 includes generating, using the at least a processor, a first set of inquiries as a function of the user profile using an inquiry machine learning model. Generating the first set of inquiries includes generally training the inquiry machine learning model using a non-user specific training data. Additionally, generating the first set of inquiries includes specifically training the inquiry machine learning model using inquiry training data, wherein the inquiry training data includes a plurality of user profiles as inputs correlated to the first set of inquiries as outputs. This may be implemented as described and with reference to FIGS. 1-7. In an embodiment, wherein the inquiry machine learning model includes a large language model. IN another embodiment, the first set of inquiries may be presented to the user using a chatbot.

Still referring to FIG. 8, at step 815, method 800 includes receiving, using the at least a processor, a first set of inquiry responses from the user as a function of the first set of inquiries. This may be implemented as described and with reference to FIGS. 1-7. In an embodiment, receiving the first set of inquiry responses comprises receiving the first set of inquiry responses from at least a sensor. In an embodiment, the method may include generating a plurality of contextual user data as a function of the user profile Still referring to FIG. 8, at step 820, method 800 includes generating, using the at least a processor, a diagnostic report as a function of the first set of inquiries and the first set of inquiry responses. This may be implemented as described and with reference to FIGS. 1-7. In an embodiment, the method may include determining a confidence score as a function the diagnostic report. The processor may then compare the confidence score to a confidence threshold. In another embodiment, the method may include generating a second set of inquiries as a function of the comparison of the confidence score to a confidence threshold; receiving a second set of inquiry responses from the user; and refining the diagnostic report as a function of the second set of inquiries and the second set of inquiry responses. Additionally, the diagnostic report may include a plurality of diagnostic data and/or a treatment plan.

Still referring to FIG. 8, at step 825, method 800 includes generating, using the at least a processor, a diagnostic report as a function of the first set of inquiries and the first set of inquiry responses. This may be implemented as described and with reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
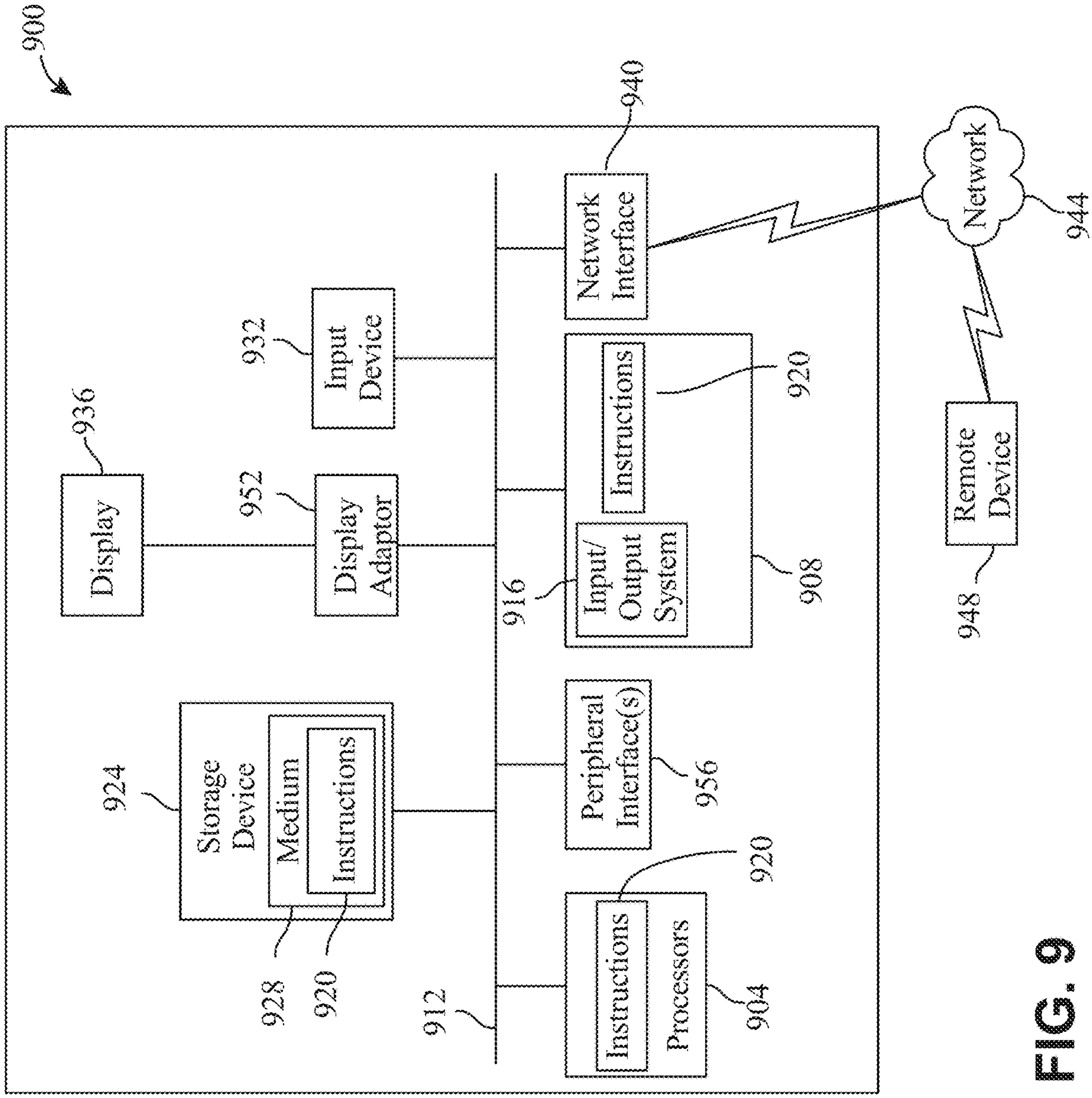
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for generating a diagnostic report, wherein the apparatus comprises:

at least a processor; and a memory communicatively connected to the at least a processor, wherein the memory contains instructions configuring the at least a processor to:

receive a user profile pertaining to a user;

extract contextual data from the user profile;

generate a set of inquiries as a function of the contextual data using an inquiry machine learning model, wherein generating the set of inquiries comprises:

training the inquiry machine learning model using inquiry training data, wherein the inquiry training data comprises a plurality of contextual data as input correlated to a plurality of inquiries as output; and generating the set of inquiries as a function of the contextual data using the trained inquiry machine learning model;

receive a set of inquiry responses from the user as a function of the set of inquiries;

update the inquiry machine learning model using the set of inquiry responses by:

applying an error function to input and output results of the inquiry machine learning model using the set of inquiry responses:

adjusting one or more weights, biases, or coefficients of the inquiry machine learning model based on the error function; and iteratively repeating the adjusting until a convergence test is satisfied;

generate a diagnostic report as a function of the set of inquiries and the set of inquiry responses; and display the diagnostic report using a display device.

2. The apparatus of claim 1, wherein the contextual data comprises a temporal attribute associated with the user profile.

3. The apparatus of claim 1, wherein the contextual data comprises a plurality of user-specific contextual attributes.

4. The apparatus of claim 3, wherein the plurality of user-specific contextual attributes comprises data describing one or more symptoms experienced by the user.

5. The apparatus of claim 1, wherein the set of inquiries comprises a set of instructions for one or more medical tests.

6. The apparatus of claim 5, wherein the set of inquiry responses comprises a recording of a performance of one or more actions by the user as directed by the set of instructions.

7. The apparatus of claim 1, wherein training the inquiry machine learning model comprises:

generally training the inquiry machine learning model using non-user specific training data; and specifically training the inquiry machine learning model using the inquiry training data.

8. The apparatus of claim 1, wherein the inquiry machine learning model comprises a large language model.

9. The apparatus of claim 1, wherein generating the diagnostic report comprises:

training a diagnostic machine learning model using training data containing a plurality of inquiries and inquiry responses as input correlated to a plurality of diagnostic report as output; and generating the diagnostic report using the trained diagnostic machine learning model.

10. The apparatus of claim 1, wherein the memory further instructs the at least a processor to:

determine a confidence score as a function of the diagnostic report; and compare the confidence score to a confidence threshold.

11. A method for generating a diagnostic report, wherein the method comprises:

receiving, using at least a processor, a user profile pertaining to a user;

extracting, using the at least a processor, contextual data from the user profile;

generating, using the at least a processor, a set of inquiries as a function of the contextual data using an inquiry machine learning model, wherein generating the set of inquiries comprises:

training the inquiry machine learning model using inquiry training data, wherein the inquiry training data comprises a plurality of contextual data as input correlated to a plurality of inquiries as output; and generating a first set of inquiries as a function of the contextual data using a trained inquiry machine learning model;

receiving, using the at least a processor, a set of inquiry responses from the user as a function of the set of inquiries;

updating, by the at least a processor, the inquiry machine learning model using the set of inquiry responses by:

applying an error function to input and output results of the inquiry machine learning model using the set of inquiry responses:

adjusting one or more weights, biases, or coefficients of the inquiry machine learning model based on the error function; and iteratively repeating the adjusting until a convergence test is satisfied;

generating, using the at least a processor, a diagnostic report as a function of the set of inquiries and the set of inquiry responses; and displaying the diagnostic report using at least a display device.

12. The method of claim 11, wherein the contextual data comprises a temporal attribute associated with the user profile.

13. The method of claim 11, wherein the contextual data comprises a plurality of user-specific contextual attributes.

14. The method of claim 13, wherein the plurality of user-specific contextual attributes comprises data describing one or more symptoms experienced by the user.

15. The method of claim 11, wherein the set of inquiries comprises a set of instructions for one or more medical tests.

16. The method of claim 15, wherein the set of inquiry responses comprises a recording of a performance of one or more actions by the user as directed by the set of instructions.

17. The method of claim 11, wherein training the inquiry machine learning model comprises:

generally training the inquiry machine learning model using non-user specific training data; and specifically training the inquiry machine learning model using the inquiry training data.

18. The method of claim 11, wherein the inquiry machine learning model comprises a large language model.

19. The method of claim 11, wherein generating the diagnostic report comprises:

training a diagnostic machine learning model using training data containing a plurality of inquiries and inquiry responses as input correlated to a plurality of diagnostic report as output; and generating the diagnostic report using the trained diagnostic machine learning model.

20. The method of claim 11, wherein the method further comprises:

determining, using the at least a processor, a confidence score as a function of the diagnostic report; and comparing, using the at least a processor, the confidence score to a confidence threshold.

* * * * *